(12) United States Patent
Routh et al.

(10) Patent No.: US 12,359,266 B2
(45) Date of Patent: Jul. 15, 2025

(54) TILED CLICKSEQ FOR TARGETED VIRUS WHOLE GENOME SEQUENCING

(71) Applicant: Board of Regents, The University of Texas System, Austin, TX (US)

(72) Inventors: Andrew Routh, Galveston, TX (US); Elizabeth Jaworski, La Marque, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 90 days.

(21) Appl. No.: 18/002,168

(22) PCT Filed: Jun. 18, 2021

(86) PCT No.: PCT/US2021/038048
§ 371 (c)(1),
(2) Date: Dec. 19, 2022

(87) PCT Pub. No.: WO2021/257963
PCT Pub. Date: Dec. 23, 2021

(65) Prior Publication Data
US 2023/0304107 A1 Sep. 28, 2023

Related U.S. Application Data

(60) Provisional application No. 63/040,869, filed on Jun. 18, 2020.

(51) Int. Cl.
*C12Q 1/68* (2018.01)
*C12Q 1/6869* (2018.01)
*C12Q 1/70* (2006.01)

(52) U.S. Cl.
CPC .......... *C12Q 1/701* (2013.01); *C12Q 1/6869* (2013.01); *C12Q 2600/156* (2013.01)

(58) Field of Classification Search
None
See application file for complete search history.

(56) References Cited

U.S. PATENT DOCUMENTS

2019/0256547 A1 8/2019 Routh
2021/0102194 A1* 4/2021 Steemers ........... C12N 15/1065

FOREIGN PATENT DOCUMENTS

WO 2015026853 A3 4/2015
WO 2021257963 A1 12/2021

OTHER PUBLICATIONS

Jaworski et al, Parallel ClickSeq and Nanopore sequencing elucidates the rapid evolution of defective-interfering RNAs in Flock House virus, PLoS Pathog May 5, 2017;13(5):e1006365. doi: 10.1371/journal.ppat.1006365. eCollection May 2017.*

(Continued)

*Primary Examiner* — Aaron A Priest
(74) *Attorney, Agent, or Firm* — Edwin S. Flores; Daniel J. Chalker; Chalker Flores, LLP

(57) ABSTRACT

The present invention includes a method and kit for single-primer tiled sequencing comprising: reverse transcribing a target nucleic acid with multiple tiled primers spaced along the genome, each only targeting one annealing site to form amplicons in the presence of terminating 3' azido nucleotides to incorporate the terminating 3' azido nucleotides into the cDNA; click-ligating a downstream primer onto tire 3' azido terminated cDNA such that a second template-specific primer is not required; amplifying the click-ligated cDNA; and sequencing the amplicons.

17 Claims, 24 Drawing Sheets

Specification includes a Sequence Listing.

(56) References Cited

OTHER PUBLICATIONS

Routh et al, ClickSeq: Fragmentation-Free Next-Generation Sequencing via Click Ligation of Adaptors to Stochastically Terminated 3'-Azido cDNAs, J Mol Biol Aug. 14, 2015;427(16):2610-6. doi: 10.1016/j.jmb.2015.06.011. Epub Jun. 24, 2015.*
Xu et al, Multiplexed Primer Extension Sequencing Enables High Precision Detection of Rare Splice Isoforms, Nat Methods. Jan. 2019;16(1):55-58. doi: 10.1038/s41592-018-0258-x. Epub Dec. 20, 2018.*
Viehweger, et al. "Direct RNA nanopore sequencing of full-length coronavirus genomes provides novel insights into structural variants and enables modification analysis" Genome Res. 2019 09;29(9):1545-54.
Vignuzzi et al. "Defective viral genomes are key drivers of the virus-host interaction" Nat Microbiol. Jun. 3, 2019.
Walker, et al. "Pilon: an integrated tool for comprehensive microbial variant detection and genome assembly improvement" PloS one. 2014;9(11):e112963.
Xie, et al. "An Infectious cDNA Clone of SARS-CoV-2" Cell Host Microbe. May 13, 2020;27(5):841-8 e3.
Yi, H. "2019 novel coronavirus is undergoing active recombination" Clin Infect Dis. Mar. 4, 2020.
Australian Patent Office, International search Report and Written Opinion for PCT/US2021/038048 dated Aug. 30, 2021, 9 pp.
Banerjee, et al. "Enhanced accumulation of coronavirus defective interfering RNA from expressed negative-strand transcripts by coexpressed positive-strand RNA transcripts" Virology. Sep. 1, 2001;287(2):286-300.
Chang, et al. "A cis-acting function for the coronavirus leader in defective interfering RNA replication" J Virol. Dec. 1994;68(12):8223-31.
Chen et al. "fastp: an ultra-fast all-in-one FASTQ preprocessor" Bioinformatics. 2018;34(17):1884-190.
Gribble, et al. The coronavirus proofreading exoribonuclease mediates extensive viral recombination. PLoS pathogens. Jan. 2021;17(1):e1009226.
Gribble, et al. "The coronavirus proofreading exoribonuclease mediates extensive viral recombination" bioRxiv. 2020:2020.04.23. 057786.
Grubaugh, et al. "An amplicon-based sequencing framework for accurately measuring intrahost virus diversity using PrimalSeq and iVar" Genome Biol. Jan. 8, 2019;20(1):8.
Grubaugh, et al. Travel Surveillance and Genomics Uncover a Hidden Zika Outbreak during the Waning Epidemic. Cell. Aug. 22, 2019;178(5):1057-71 e11.
Guo, et al. "Rapid cost-effective viral genome sequencing by V-seq" bioRxiv. 2020:2020.08.15.252510.
Gussow, et al. "Genomic determinants of pathogenicity in SARS-CoV-2 and other human coronaviruses". Proc Natl Acad Sci U S A. Jun. 30, 2020;117(26):15193-9.
Hadfield, et al. "Nextstrain: real-time tracking of pathogen evolution" Bioinformatics. Dec. 1, 2018;34(23):4121-3.
Harcourt, et al. "Isolation and characterization of SARS-CoV-2 from the first US COVID-19 patient" bioRxiv. Mar. 7, 2020.
Harcourt, et al. "Severe Acute Respiratory Syndrome Coronavirus 2 from Patient with Coronavirus Disease" United States. Emerg Infect Dis. Jun. 2020;26(6):1266-73.
Itokawa, et al. "Disentangling primer interactions improves SARS-CoV-2 genome sequencing by multiplex tiling PCR" PloS one. 2020;15(9):e0239403.
Jaworski, et al. "ClickSeq: Replacing Fragmentation and Enzymatic Ligation with Click-Chemistry to Prevent Sequence Chimeras" Methods Mol Biol. 2018;1712:71-85.
Johnson, et al. "Loss of furin cleavage site attenuates SARS-CoV-2 pathogenesis" Nature. Jan. 25, 2021.
Joo, et al. "Replication of murine coronavirus defective interfering RNA from negative-strand transcripts" J Virol. Sep. 1996;70(9):5769-76.
Kemp, et al. "Recurrent emergence and transmission of a SARS-CoV-2 Spike deletion ?H69/V70" bioRxiv.2020:2020.12.14. 422555.
Kim, et al. "Generation and selection of coronavirus defective interfering RNA with large open reading frame by RNA recombination and possible editing" Virology. May 1993;194(1):244-53.
Kim, et al. "The Architecture of SARS-CoV-2 Transcriptome" Cell. Apr. 18, 2020.
Klimstra, et al. "SARS-CoV-2 growth, furin-cleavage-site adaptation and neutralization using serum from acutely infected, hospitalized COVID-19 patients" bioRxiv. 2020:2020.06.19.154930.
Knyazev, et al. "CliqueSNV: An Efficient Noise Reduction Technique for Accurate Assembly of Viral Variants from NGS Data" bioRxiv. 2020:264242.
Langmead, et al. "Fast gapped-read alignment with Bowtie 2" Nature methods. Mar. 4, 2012;9(4):357-9.
Li, H. "Minimap and miniasm: fast mapping and de novo assembly for noisy long sequences" Bioinformatics. Jul. 15, 2016;32(14):2103-10.
Makino, et al. "Defective interfering particles of mouse hepatitis virus" Virology. Feb. 1984;133(1):9-17.
Makino, et al. "Defective-interfering particles of murine coronavirus: mechanism of synthesis of defective viral RNAs" Virology. Mar. 1988;163(1):104-11.
Makino, et al. "Primary structure and translation of a defective interfering RNA of murine coronavirus" Virology. Oct. 1988;166(2):550-60.
Makino, et al. "Structure of the intracellular defective viral RNAs of defective interfering particles of mouse hepatitis virus" J Virol. May 1985;54(2):329-36.
Martin, M. "Cutadapt removes adapter sequences from high-throughput sequencing reads" EMBnetjournal. 2011;17:10-2.
Milne, et al. "Tablet—next generation sequence assembly visualization" Bioinformatics. Feb. 1, 2010;26(3):401-2.
Muth, et al. "Attenuation of replication by a 29 nucleotide deletion in SARS-coronavirus acquired during the early stages of human-to-human transmission" Scientific reports. Oct. 11, 2018;8(1):15177.
Ogando, et al. "SARS-coronavirus-2 replication in Vero E6 cells: replication kinetics, rapid adaptation and cytopathology". bioRxiv. 2020:2020.04.20.049924.
Parker, et al. "periscope: sub-genomic RNA identification in SARS-CoV-2 Genomic Sequencing Data" bioRxiv. 2020:2020.07.01. 181867.
Penzes, et al. "Generation of a defective RNA of avian coronavirus infectious bronchitis virus (IBV)" Defective RNA of coronavirus IBV. Adv Exp Med Biol. 1995;380:563-9.
Plante, et al. "Spike mutation D614G alters SARS-CoV-2 fitness and neutralization susceptibility" bioRxiv. Sep. 2, 2020.
Plante, et al. "The Variant Gambit: COVIDs Next Move" Cell Host Microbe. 2021 Mar. 1, 2021.
Quick, et al. "Multiplex PCR method for MinION and Illumina sequencing of Zika and other virus genomes directly from clinical samples", Nature Protocols, 2017, vol. 12, No. 6, pp. 1261-1276.
Quinlan, AR. "BEDTools: The Swiss-Army Tool for Genome Feature Analysis" Curr Protoc Bioinformatics. Sep. 8, 2014;47:11 2 1-34.
Routh, A., et al. "ClickSeq: Fragmentation-Free Next-Generation Sequencing via Click Ligation of Adaptors to Stochastically Terminated 3-Azido cDNAs" (author manuscript), Journal of Molecular Biology, 2015, vol. 427, No. 16, pp. 2610-2616. pp. 1, 3.
Routh, et al. "ClickSeq: Fragmentation-Free Next-Generation Sequencing via Click Ligation of Adaptors to Stochastically Terminated 3-Azido cDNAs" J Mol Biol. Aug. 14, 2015;427(16):2610-6.
Routh, et al. "CoVaMa: Co-Variation Mapper for disequilibrium analysis of mutant loci in viral populations using next-generation sequence data" Methods. Sep. 25, 2015.
Routh, et al. "Discovery of functional genomic motifs in viruses with ViReMa—a Virus Recombination Mapper—for analysis of next-generation sequencing data" Nucleic Acids Res. Jan. 2014;42(2):e11.
Routh, et al. Poly(A)-ClickSeq: click-chemistry for next-generation 3-end sequencing without RNA enrichment or fragmentation. Nucleic Acids Res. Jul. 7, 2017;45(12):e112.

(56) References Cited

OTHER PUBLICATIONS

Smith, et al. "Coronaviruses as DNA wannabes: a new model for the regulation of RNA virus replication fidelity" PLoS pathogens. 2013;9(12):e1003760.

Smith, et al. "UMI-tools: modeling sequencing errors in Unique Molecular Identifiers to improve quantification accuracy" Genome Res. Mar. 2017;27(3):491-9.

Su, et al. "Discovery of a 382-nt deletion during the early evolution of SARS-CoV-2" bioRxiv. 2020:2020.03.11.987222.

Tyson, et al. Improvements to the ARTIC multiplex PCR method for SARS-CoV-2 genome sequencing using nanopore. bioRxiv. Sep. 4, 2020.

* cited by examiner

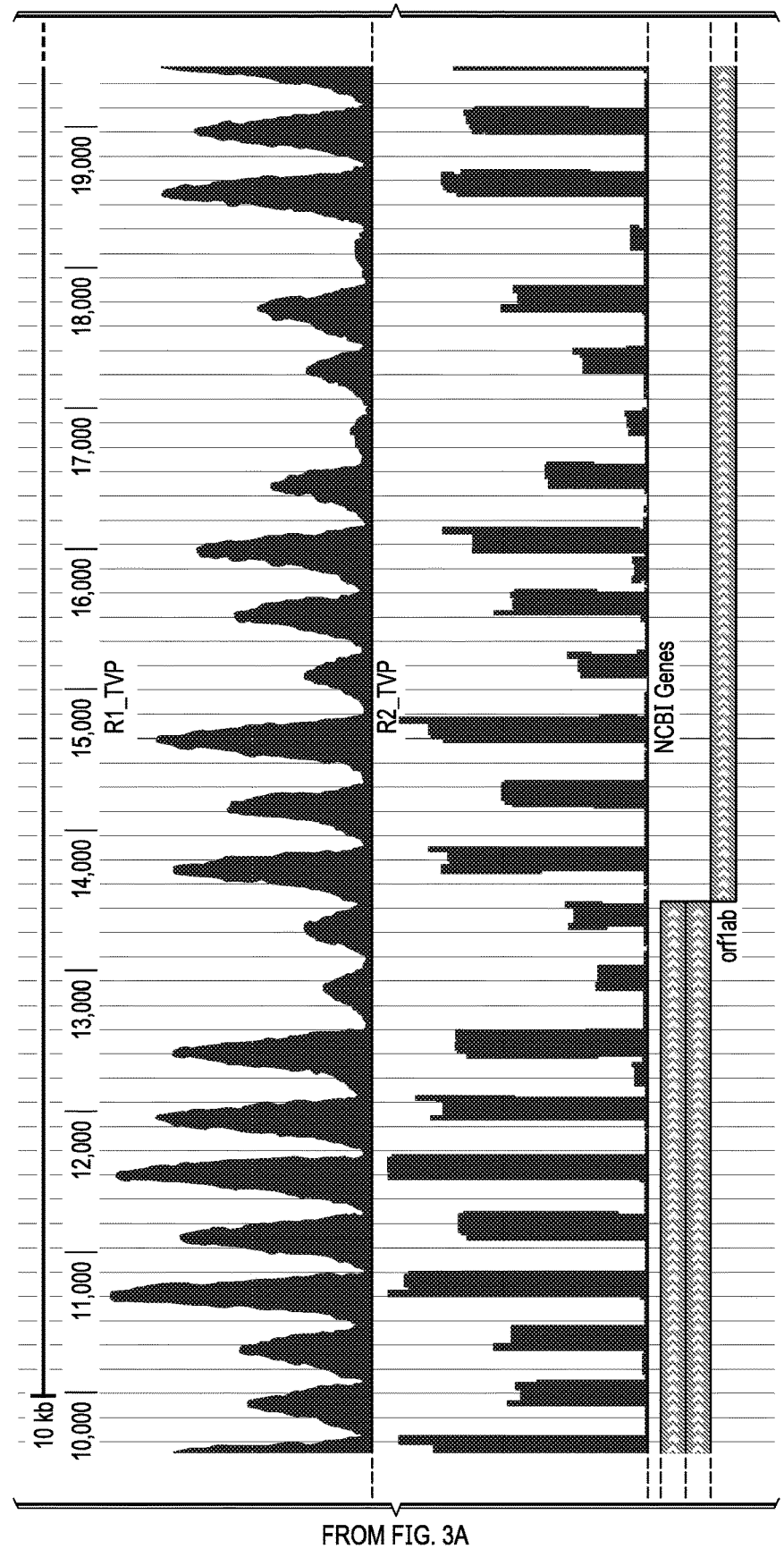

SARS-CoV-2 genome schematic

Paired-primer scheme

Tiled-ClickSeq primer scheme

ClickSeq NGS library synthesis

Tiled-ClickSeq Read

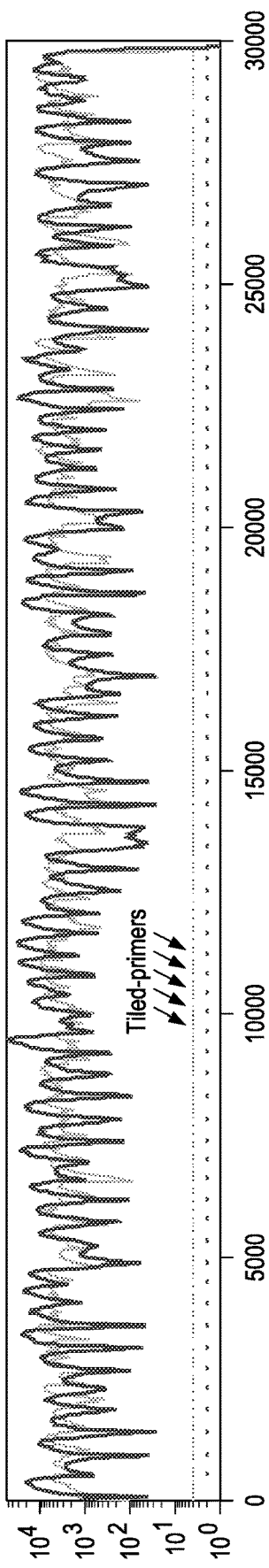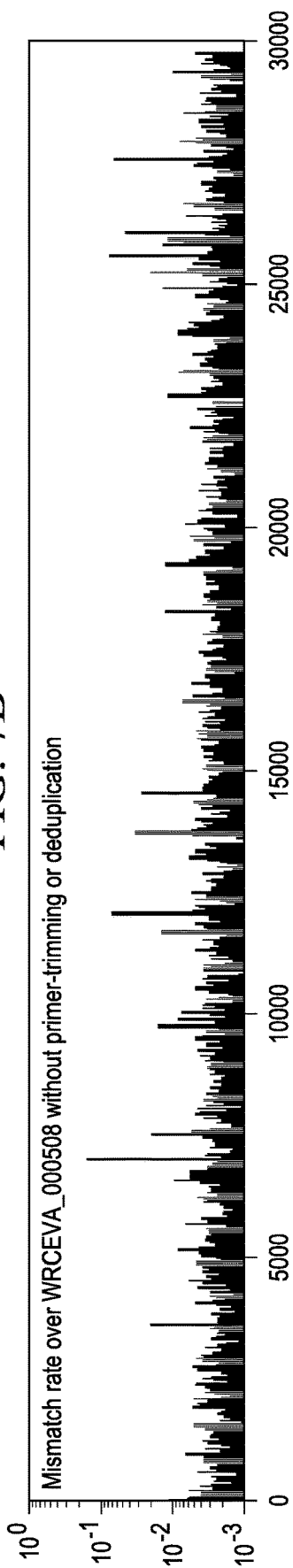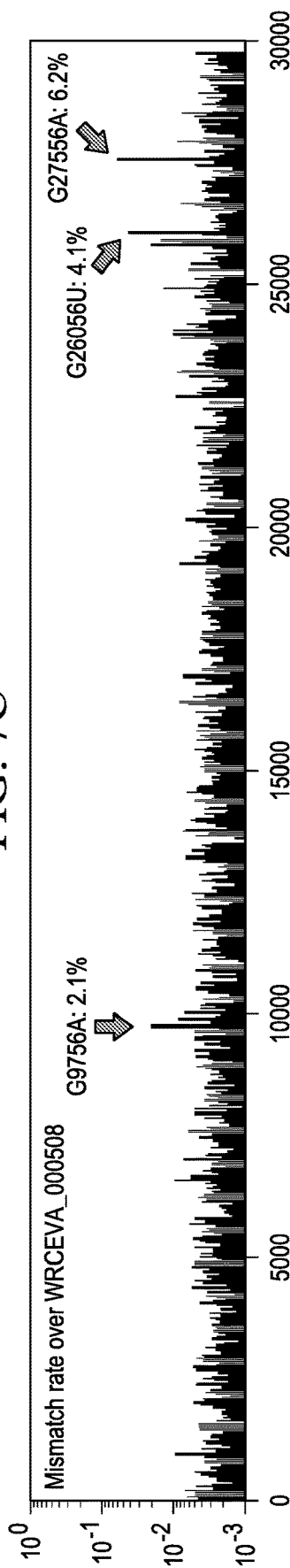
FIG. 7A
FIG. 7B
FIG. 7C

A) RNA recombination event frequencies

| | TVP23155 | WT-SN | Wt-Cellular | PRRA-SN | PRRA-Cellular | WRCEVA_00501 | WRCEVA_00502 | WRCEVA_00503 | WRCEVA_00504 | WRCEVA_00505 | WRCEVA_00506 | WRCEVA_00507 | WRCEVA_00508 | WRCEVA_00509 | WRCEVA_00510 | WRCEVA_00511 | WRCEVA_00512 | WRCEVA_00513 | WRCEVA_00514 | WRCEVA_00515 | WRCEVA_00516 |
|---|---|---|---|---|---|---|---|---|---|---|---|---|---|---|---|---|---|---|---|---|---|
| *:70_21054 | 0.11 | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 |
| Spike:70_21557 | 2.0 | 0.0 | 11.21 | 0.71 | 8.51 | 1.73 | 7.34 | 3.66 | 3.88 | 1.99 | 10.06 | 2.85 | 9.03 | 4.88 | 2.96 | 3.31 | 1.98 | 1.26 | 2.82 | 0.7 | 1.61 |
| ORF3a:70_25386 | 0.0 | 0.95 | 88.27 | 1.2 | 90.34 | 1.55 | 7.98 | 4.08 | 3.38 | 2.76 | 8.21 | 5.88 | 7.55 | 4.69 | 4.41 | 4.13 | 3.96 | 1.01 | 3.0 | 1.76 | 1.55 |
| E:70_26238 | 0.0 | 0.0 | 5.77 | 0.0 | 9.27 | 0.49 | 0.92 | 0.61 | 0.6 | 0.18 | 1.28 | 0.86 | 1.06 | 0.52 | 0.35 | 0.61 | 0.44 | 0.16 | 0.38 | 0.24 | 0.3 |
| M:70_26474 | 7.48 | 0.0 | 24.84 | 0.39 | 32.21 | 4.26 | 9.86 | 3.54 | 3.55 | 3.33 | 12.94 | 7.26 | 11.84 | 4.69 | 3.21 | 3.33 | 6.92 | 2.66 | 2.87 | 1.74 | 2.86 |
| ORF6:70_27042 | 0.0 | 0.0 | 0.0 | 0.81 | 9.91 | 0.47 | 0.55 | 1.03 | 0.82 | 0.17 | 0.59 | 0.51 | 0.74 | 0.48 | 0.37 | 0.77 | 0.64 | 0.28 | 0.81 | 0.12 | 0.33 |
| ORF7a:70_27389 | 6.69 | 0.0 | 3.09 | 0.0 | 4.01 | 1.21 | 5.69 | 3.94 | 3.74 | 1.72 | 4.4 | 2.43 | 7.22 | 3.25 | 2.96 | 2.77 | 3.89 | 1.78 | 2.46 | 2.13 | 1.83 |
| ORF8:70_27889 | 2.09 | 0.3 | 6.01 | 0.0 | 4.74 | 0.0 | 0.0 | 0.77 | 1.47 | 0.0 | 0.0 | 3.11 | 0.0 | 1.19 | 0.0 | 0.0 | 0.67 | 0.0 | 1.19 | 0.44 | 1.18 |
| N:70_28261 | 2.48 | 0.33 | 2.04 | 0.13 | 2.04 | 1.96 | 6.52 | 3.63 | 3.32 | 3.02 | 10.07 | 6.05 | 4.03 | 3.3 | 3.07 | 2.67 | 2.94 | 1.24 | 2.27 | 1.58 | 2.18 |
| 23583_23599 | 0.07 | 0.77 | 0.47 | 0.0 | 0.0 | 0.0 | 0.0 | 53.33 | 0.17 | 0.0 | 0.0 | 0.0 | 0.0 | 2.29 | 0.0 | 4.01 | 0.16 | 0.09 | 0.4 | 0.09 | 0.36 |
| 23603_23616 | 0.0 | 0.0 | 0.0 | 97.85 | 97.31 | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 |
| 27619_27642 | 0.0 | 0.0 | 0.0 | 0.0 | 0.0 | 0.0 | 0.0 | 3.46 | 0.0 | 0.0 | 0.0 | 0.0 | 0.0 | 0.0 | 0.0 | 0.0 | 0.0 | 0.0 | 0.0 | 0.0 | 0.0 |

FIG. 8A

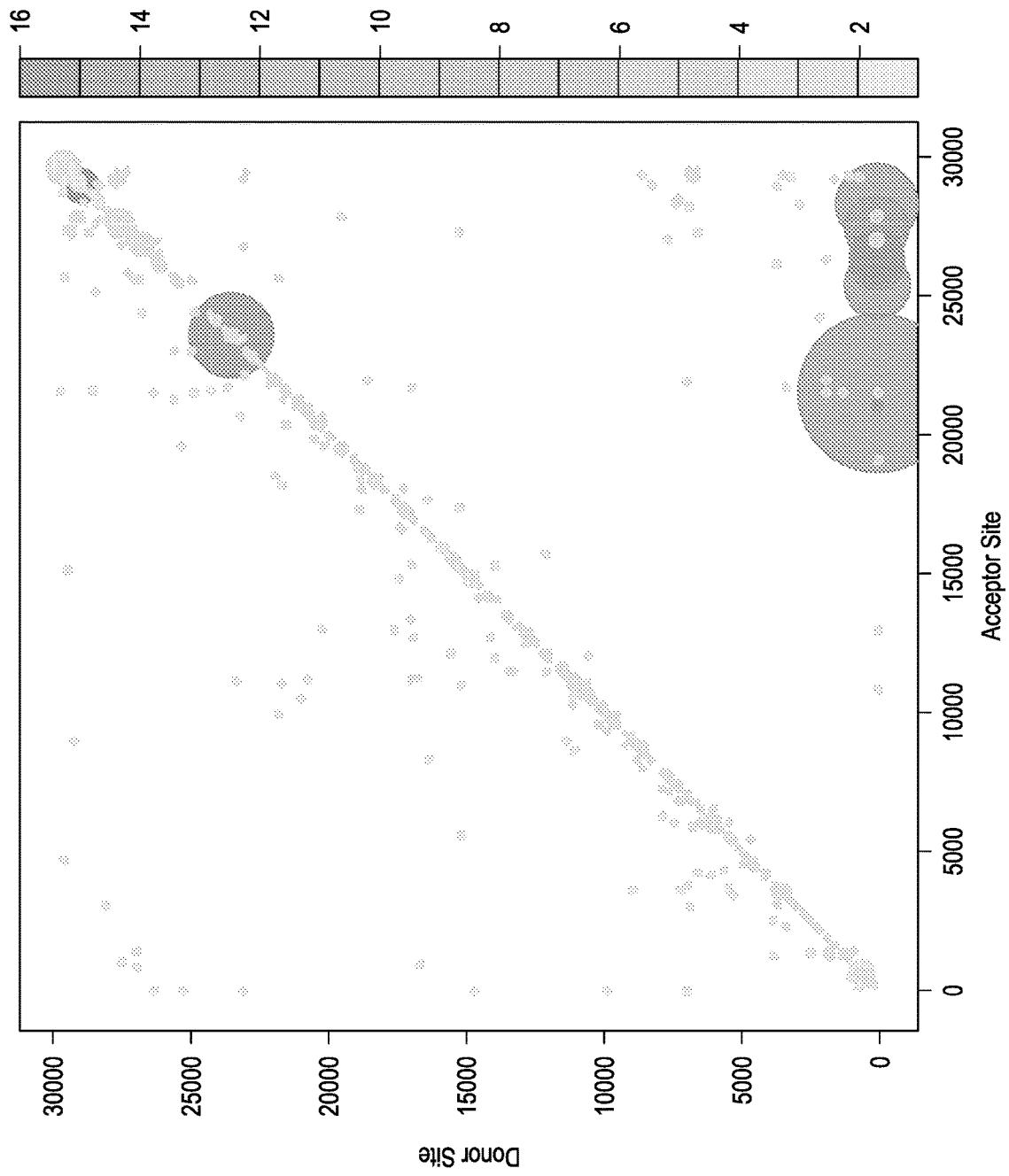

SEQUENCE LISTING

<160> NUMBER OF SEQ ID NOS: 2

<210> SEQ ID NO 1
<211> LENGTH: 34
<212> TYPE: DNA
<213> ORGANISM: Artificial Sequence
<220> FEATURE:
<223> OTHER INFORMATION: Synthetic

```
<400> SEQUENCE: 1
gtgactggag ttcagacgtg tgctcttccg atct                           34

<210> SEQ ID NO 2
<211> LENGTH: 22
<212> TYPE: DNA
<213> ORGANISM: Artificial Sequence
<220> FEATURE:
<223> OTHER INFORMATION: Synthetic

<400> SEQUENCE: 2
tgtctcacca ctacgaccgt ac                                        22
```

US 12,359,266 B2

TILED CLICKSEQ FOR TARGETED VIRUS WHOLE GENOME SEQUENCING

CROSS-REFERENCE TO RELATED APPLICATIONS

This application is a National Stage of International Application No. PCT/US2021/038048, filed Jun. 18, 2021, which claims the benefit of U.S. Provisional Application No. 63/040,869, filed Jun. 18, 2020. The contents of each of which are incorporated by reference in their entirety.

TECHNICAL FIELD OF THE INVENTION

The present invention relates in general to the field of sequencing, and more particularly, to the sequencing of whole or partial genomes, exomes, or bacteria sequencing. e.g., viral or bacterial genomes.

STATEMENT OF FEDERALLY FUNDED RESEARCH

None.

BACKGROUND OF THE INVENTION

Without limiting the scope of the invention, its background is described in connection with the sequencing of genomes.

Whole genome sequencing of virus isolates from clinical or field samples is a critical aspect of epidemiology and surveillance. Particularly during the course of an outbreak or pandemic, it allows researchers and doctors to trace to origin and transmission of individual species of viruses between their host as well as determine whether and how the virus is evolving or adapting to its host over time. There are many examples of large scale whole viral genome sequencing efforts including during regular flu seasons, the Ebola outbreak and the current SARS-CoV2 pandemic.

The present inventors have previously disclosed, in U.S. Patent No. 20190256547, a method and kit for cDNA synthesis of a 3'UTR/poly(A) tail junction of cellular RNA comprising: obtaining RNA comprising a 3'UTR/poly(A) junction and a poly(a) tail; combining the RNA with three terminating nucleotides of modified-deoxyGTP, modified-deoxyCTP and modified-deoxyATP, dNTPs, and adaptor sequence-oligo-dT; performing reverse transcription of the RNA with a reverse transcriptase primed with the adaptor sequence-oligo-dT to form terminated cDNA fragments that are stochastically terminated upstream of the 3'UTR/poly(A) junction, but not within the poly(A) tail; isolating the terminated cDNA fragments; chemically ligating a functionalized 5' adaptor to the terminated cDNA; and amplifying the chemically-ligated cDNA into an amplification product, wherein the cDNA is enriched for sequences at the 3'UTR/poly(A) tail junction without fragmentation or enzymatic ligation.

However, despite these advances, a need remains for rapid, accurate, and reproducible partial or whole genome sequencing, specifically, for viral genome sequencing.

SUMMARY OF THE INVENTION

In one embodiment, the present invention includes a method of single-primer-per-amplicon tiled sequencing comprising: reverse transcribing a target nucleic acid with multiple tiled primers spaced along a genome, each only targeting one annealing site to form amplicons, in the presence of terminating 3' azido nucleotides to incorporate the terminating 3' azido nucleotides into the cDNA; click-ligating a downstream primer onto the 3' azido terminated cDNA such that a template-specific primer is not required; amplifying the click-ligated cDNA; and sequencing the amplicons. In one aspect, the target nucleic acid is a partial or whole viral or bacterial genome or a sub-genomic viral genome. In another aspect, the target nucleic acid is a whole genome or a sub-genomic genome or an RNA or DNA transcript derived from the parental genome. In another aspect, the target is a host or metazoan RNA or a messenger RNA. In another aspect, the target nucleic acid is either deoxyribonucleic acid (DNA) or ribonucleic acid (RNA). In another aspect, the amplification reaction is a PCR or iso-thermal amplification reaction, or wherein the amplification step occurs without the need to design corresponding paired PCR or iso-thermal amplification reaction primers. In another aspect, the sequencing is by an automated process on a chip, Sanger sequencing, Maxam-Gilbert sequencing, dye terminator sequencing, sequencing by synthesis, pyrosequencing, microarray hybridization, next-generation sequencing methods, next-next-generation sequencing, ion semiconductor sequencing, polony sequencing, sequencing by ligation, DNA nanoball sequencing, or single molecule sequencing. In another aspect, the amplicons are 100-10,000 nucleotides in length. In another aspect, the method only requires one template-specific primer per amplicon. In another aspect, the sequences of the multiple tiled primer sequences are selected along the virus or bacterial genome. In another aspect, the sequences of the multiple tiled primer sequences are selected along two or more different viral or bacterial genomes in parallel. In another aspect, the sequences of the multiple tiled primer sequences only target one annealing site. In another aspect, the target nucleic acid is sequenced without the need to design corresponding paired PCR primers. In another aspect, the downstream primer comprises a unique molecular identifier, which is a sequence such as a barcode that allows for identification of the individual downstream primer or click-adaptor.

In another embodiment, the present invention includes a method of single-primer tiled whole or partial viral genome or multiple genome, sequencing comprising: reverse transcribing a target viral nucleic acid with multiple tiled primers spaced along the whole or partial viral genome, or multiple genomes, each only targeting one annealing site to form amplicons in the presence of terminating 3' azido nucleotides to incorporate the terminating 3' azido nucleotides into the cDNA; click-ligating a downstream primer onto the 3' azido terminated viral cDNA such that a template-specific primer is not required; amplifying the click-ligated cDNA and sequencing the amplicons for the whole or partial viral genome. In another aspect, the amplification reaction is a PCR, or other iso-thermal amplification reaction, or wherein the amplification step occurs without the need to design corresponding paired PCR, or other iso-thermal amplification reaction primers. In another aspect, the sequencing is by an automated process on a chip, Sanger sequencing, Maxam-Gilbert sequencing, dye terminator sequencing, sequencing by synthesis, pyrosequencing, microarray hybridization, next-generation sequencing methods, next-next-generation sequencing, ion semiconductor sequencing, polony sequencing, sequencing by ligation, DNA nanoball sequencing, or single molecule sequencing. In another aspect, the amplicons are 100-10,000 nucleotides in length. In another aspect, the method only requires one template-specific primer per amplicon. In another aspect, the sequences of the multiple tiled primer sequences are selected along the viral or bacterial genome. In another aspect, the sequences of the multiple tiled primer sequences are selected along two or more different viral or bacterial genomes in parallel. In another aspect, the sequences of the multiple tiled primer sequences only target one annealing site. In another aspect, the target nucleic acid is sequenced without the need to design corresponding paired PCR primers. In another aspect, the downstream primer comprises a unique molecular identifier. In another aspect, the downstream primer comprises a unique molecular identifier, which is a sequence such as a barcode that allows for identification of the individual downstream primer or click-adaptor.

In another embodiment, the present invention includes a kit for cDNA synthesis of a genome or multiple genomes using single-primer tiled sequencing comprising: one or more vials comprising: nucleotides of modified-deoxyGTP, modified-deoxyCTP, modified-deoxyTTP and modified-deoxyATP, dNTPs, and adaptor sequence-oligo-dT; a cDNA fragment isolating kit; one or more vials comprising components for chemically ligating a functionalized 5' adaptor to the cDNA; a DNA amplification kit comprising for amplifying the chemically-ligated cDNA into an amplification product; one or more multiple tiled primers spaced along the genome or multiple genomes, each only targeting one annealing site to form amplicons; and instructions for amplification of the RNA 3' end and one or more multiple tiled primers spaced along the genome or multiple genomes. In one aspect, the target nucleic acid is a whole viral genome or a sub-genomic viral genome or multiple genomes. In another aspect, the target nucleic acid is a whole genome or a sub-genomic genome or an RNA or DNA transcript derived from the parental genome. In another aspect, the target nucleic acid is either deoxyribonucleic acid (DNA) or ribonucleic acid (RNA). In another aspect, the terminating modified-deoxyGTP, modified-deoxyCTP, modified-deoxyTTP and modified-deoxyATP are 2'- or 3'-azido-nucleotides (AzGTP, AzCTP, AzTTP and AzATP) or 3'-(0-Propargyl)-NTPs that pair with an alkyne or azide modified oligo during the 'click' reaction is a hexynyl-oligo or azide-oligo. In another aspect, a ratio of the four or fewer of 2'- or 3'-azido-nucleotides (AzGTP, AzCTP, AzTTP and AzATP), or propargyl-GTP, propargyl-CTP, propargyl-TTP or propargyl-ATP, to dNTPs is 1:250, 1:249, 1:248, 1:247, 1:246, 1:245, 1:244, 1:243, 1:242, 1:241, 1:240, 1:239, 1:238, 1:237, 1:236, 1:235, 1:234, 1:233, 1:232, 1:231, 1:230, 1:229, 1:228, 1:227, 1:226, 1:225, 1:224, 1:223, 1:222, 1:221, 1:220, 1:219, 1:218, 1:217, 1:216, 1:215, 1:214, 1:213, 1:212, 1:211, 1:210, 1:209, 1:208, 1:207, 1:206, 1:205, 1:204, 1:203, 1:202, 1:201, 1:200, 1:199, 1:198, 1:197, 1:196, 1:195, 1:194, 1:193, 1:192, 1:191, 1:190, 1:189, 1:188, 1:187, 1:186, 1:185, 1:184, 1:183, 1:182, 1:181, 1:180, 1:179, 1:178, 1:177, 1:176, 1:175, 1:174, 1:173, 1:172, 1:171, 1:170, 1:169, 1:168, 1:167, 1:166, 1:165, 1:164, 1:163, 1:162, 1:161, 1:160, 1:159, 1:158, 1:157, 1:156, 1:155, 1:154, 1:153, 1:152, 1:151, 1:150, 1:149, 1:148, 1:147, 1:146, 1:145, 1:144, 1:143, 1:142, 1:141, 1:140, 1:139, 1:138, 1:137, 1:136, 1:135, 1:134, 1:133, 1:132, 1:131, 1:130, 1:129, 1:128, 1:127, 1:126, 1:125, 1:124, 1:123, 1:122, 1:121, 1:120, 1:119, 1:118, 1:117, 1:116, 1:115, 1:114, 1:113, 1:112, 1:111, 1:110, 1:109, 1:108, 1:107, 1:106, 1:105, 1:104, 1:103, 1:102, 1:101, 1:100, 1:99, 1:98, 1:97, 1:96, 1:95, 1:94, 1:93, 1:92, 1:91, 1:90, 1:89, 1:88, 1:87, 1:86, 1:85, 1:84, 1:83, 1:82, 1:81, 1:80, 1:79, 1:78, 1:77, 1:76, 1:75, 1:74, 1:73, 1:72, 1:71, 1:70, 1:69, 1:68, 1:67, 1:66, 1:65, 1:64, 1:63, 1:62, 1:61, 1:60, 1:59, 1:58, 1:57, 1:56, 1:55, 1:54, 1:53, 1:52, 1:51, 1:50, 1:49, 1:48, 1:47, 1:46, 1:45, 1:44, 1:43, 1:42, 1:41, 1:40, 1:39, 1:38, 1:37, 1:36, 1:35, 1:34, 1:33, 1:32, 1:31, 1:30, 1:29, 1:28, 1:27, 1:26, 1:25, 1:24, 1:23, 1:22, 1:21, 1:20, 1:19, 1:18, 1:17, 1:16, 1:15, 1:14, 1:13, 1:12, 1:11, 1:10, 1:9, 1:8, 1:7, 1:6, 1:5, 1:4, 1:3, 1:2, 0.5:0.5, or 1 mM; 1 mM, or wherein a ratio of AzGTP:AzCTP:AzTTP:AzATP is w:x:y:z, wherein w is 0.1-2.0, x is 0.1-2.0, y is 0.1-2.0, and z is 0.1-2.0. In another aspect, the kit further comprises a cDNA purification kit for purifying the cDNA away from the 2' or 3'-azido-nucleotides after the reverse transcription and before the amplification step selected from a column separation kit, magnetic bead separation kit, or streptavidin magnetic bead kit. In another aspect, the kit further comprises a clicked-cDNA-adaptor purification kit for separating the clicked-cDNA-adaptor away from unligated alkyne-functionalized 5' adaptors before the amplification step selected from a column separation kit, magnetic bead separation kit, or streptavidin magnetic bead kit. In another aspect, the click-ligating components comprise: an alkyne-functionalized 5' adaptor to the azido-terminated cDNA; a buffered solution comprising: a solvent mix comprising DMSO, water, and ethanol; metal catalysts selected from copper and ruthenium; a chelating ligand; and an accelerant. In another aspect, the click-ligating components comprise: an azide-functionalized 5' adaptor to the alkyne-terminated cDNA; a buffered solution comprising: a solvent mix comprising DMSO, water, and ethanol; metal catalysts selected from copper and ruthenium; a chelating ligand; and an accelerant. In another aspect, the reverse transcriptase (RT) is an RT derived from Avian Myeloblastosis Virus Reverse Transcriptase, Respiratory Syncytial Virus Reverse Transcriptase, Moloney Murine Leukemia Virus Reverse Transcriptase, Human Immunodeficiency Virus Reverse Transcriptase, Equine Infectious Anemia Virus Reverse Transcriptase, Rous-Associated Virus 2 Reverse Transcriptase, Avian Sarcoma Leukosis Virus Reverse Transcriptase, RNaseH (−) Reverse Transcriptase, SuperScript II Reverse Transcriptase, SuperScript III Reverse Transcriptase, SuperScript IV Reverse Transcriptase, thermostable group II intron reverse transcriptases (TGIRT), Terminator DNA Polymerase, or ThermoScript Reverse Transcriptase, wherein an RNase H activity of these RTs is present, reduced or not present. In another aspect, a selectivity of the reverse transcription and/or amplification, preferably a polymerase chain reaction, is increased by using trehalose, betaine, tetramethylammonium chloride, tetramethylammonium oxalate, formamide and oligo-blockers, or dimethylsulfoxide during the polymerase chain reaction, to reduce the occurrence of mispriming. In another aspect, the kit further comprises a sequencing kit determining an identity or sequence of the amplification products by an automated process on a chip, Sanger sequencing, Maxam-Gilbert sequencing, dye terminator sequencing, sequencing by synthesis, pyrosequencing, microarray hybridization, next-generation sequencing methods, next-next-generation sequencing, ion semiconductor sequencing, polony sequencing, sequencing by ligation, DNA nanoball sequencing, or single molecule sequencing. In another aspect, a DNA polymerase used for the amplification reaction is Taq DNA polymerase, Tfl DNA polymerase, a Taq DNA polymerase, a Klenow fragment, Sequenase or Klentaq an enzyme with proof reading activity, preferably selected from the PFU, Ultma, Vent, Deep Vent, PWO, or Tli polymerases. In another aspect, the kit further comprises a kit for purifying a PCR product from the step of amplifying the clicked-cDNA step with a column or beads. In another aspect, the wherein the downstream primer comprises a unique molecular identifier.

In another aspect, the wherein the downstream primer comprises a unique molecular identifier, which is a sequence such as a barcode that allows for identification of the individual downstream primer or click-adaptor.

BRIEF DESCRIPTION OF THE DRAWINGS

For a more complete understanding of the features and advantages of the present invention, reference is now made to the detailed description of the invention along with the accompanying figures and in which:

FIG. 1A) Coronavirus genome is a single-stranded positive sense RNA genome with a poly(A)-tail. Multiple sub-genomic mRNAs are generated through discontinuous replication and can account for the majority of virus genetic material. FIG. 1B) Tiled approaches for whole virus genome sequencing require carefully designed compatible pairs of forward (left) and reverse (right) primers. For long reads, new pairs must be designed spaced further apart. In Tiled-ClickSeq, only one templated primer is required, with the left end generated through stochastic termination of the reverse transcription reaction. FIG. 1C) The predicted read coverage of Tiled-ClickSeq data over the virus genome is illustrated for short and long reads (LR) for the left hand read derived from the azido ($N_3$) end or for the right hand read derived from the tiled primer.

FIG. 1A) Schematic of SARS-CoV-2 genome with two examples of sub-genomic mRNAs. FIG. 1B) Paired-primer approaches typically generate short amplicons flanked by upstream and downstream primers that are PCR amplified in non-overlapping pools. FIG. 1C) Tiled-ClickSeq uses a single pool of primers at the reverse-transcription step with the upstream site generated by stochastic termination by azidonucleotides. FIG. 1D) 3'-azido-blocked single-stranded cDNA fragments are 'click-ligated' using copper-catalyzed azide alkyne cycloaddition (CuAAC) to hexynyl functionalized Illumina i5 sequencing adaptors. Triazole-linked ssDNA is PCR amplified to generate a final cDNA library. FIG. 1E) The structure of the final cDNA is illustrated indicating the presence of the i5 and i7 adaptors, the 12N unique molecular identifier (UMI), the expected location of the triazole linkage, and the origins of the cDNA in the reads including the tiled primer-derived DNA, which is captured using paired-end sequencing. The hypothetical read coverage over a viral genome is as shown in FIG. 1C, yielding overlapping 'saw-tooth' patterns of sequencing coverage. Longer fragment lengths with more extensive overlapping can be obtained using decreased AzNTP:dNTP ratios. Final cDNA libraries are analyzed and size-selected by gel electrophoresis (2% agarose gel). Duplicates of libraries synthesized from 8, 80 and 800 ng of input SARS-CoV-2 RNA input are shown. FIG. 4H shows a flowchart of the data processing and bioinformatic pipeline.

FIG. 6A) Read coverage is depicted over the 5' UTR of the SARS-CoV-2 genome for each isolate revealing capture of this region. The 5-most primer from the ARTICv3 protocol at nts-30-54 is illustrated. FIG. 6B) Snapshot of read data from Tiled-ClickSeq is depicted using the Tablet Sequencing Viewer from WRCEVA_000508 over the same region of the 5'UTR as FIG. 6A). The most common single nucleotide variants (SNVs) found in complete genome reconstructions from all 12 isolates are illustrated and color-coded to depict the underlying viral protein. FIG. 6C) Phylogenetic tree of 12 WRCEVA isolates with their corresponding clade indicated.

FIGS. 7A to 7C show additional tiled-primers improves read coverage and allows identification of minority variants: FIG. 7A) Read coverage obtained from Tiled-ClickSeq over the whole viral genome is depicted using an Illumina MiSeq when using the original primers as in FIG. 2 (v1—solid) or with an additional 326 tiled-primers (v3—dotted). Tiled-primers are indicated at the bottom of the plot by short solid (v1) or dotted (v3) lines. FIG. 7B) The rates of mismatching nucleotides found in mapped NGS reads is depicted across the SARS-CoV-2 genome for isolate WRECVA_000508 prior to trimming the tiled primers from forward/'R1' reads and without PCR deduplication. FIG. 7C) The rates of mismatching is also depicted after data quality processing to remove PCR duplicates and primer-derived nucleotides in the reads, revealing 3 minority variants in this sample with frequencies >2%.

FIGS. 8A and 8B show that tiled-ClickSeq identifies sub-genomic mRNAs, structural variants and Defective-RNAs: FIG. 8A) A table of the most common RNA recombination events found using Tiled-ClickSeq in this study. The recombination junctions are indicated on the left of the table, with their relative frequencies indicated in the table and color-matched for each sample analyzed. All canonical sgmRNAs are found with their open-reading frame (ORF) indicated, in addition to one non-canonical sgmRNAs (*). Three common structural variants including two deletions in spike protein and a deletion in ORF7a were also detected. FIG. 8B) Unique RNA recombination events are plotted for 16 WRCEVA isolates as a scatter plots whereby the upstream 'donor' site is plotted on the y-axis and a downstream 'acceptor' site is plotted on x axis. The read count for each unique RNA recombination event is indicated by the size of the point, while the number of samples in which this each RNA recombination event is found is indicated by the color. Insertions/duplication/back-splicing events are found above the x=y axis, while deletions and RNA recombination events yielding sgmRNAs are found below.

DETAILED DESCRIPTION OF THE INVENTION

Figure 1A:
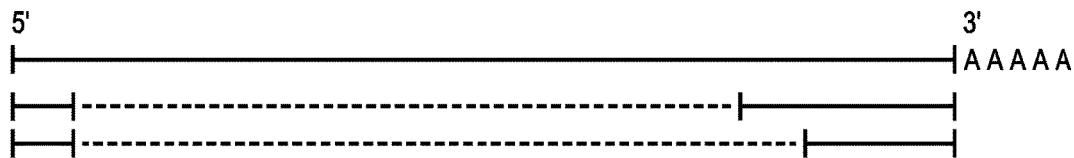
FIGS. 1A to 1C shows a schematic of tiled approaches for whole genome sequencing (WGS) of target virus.

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity but include the general class of which a specific example may be used for illustration. The terminology herein is used to describe specific embodiments of the invention, but their usage does not limit the invention, except as outlined in the claims.

Typically, whole genome sequencing is achieved through non-targeted (random) next-generation sequencing of virus isolates amplified in cell culture or directly from patient samples. However, in cases were virus isolation and amplification is not feasible the virus must be directly sequenced from its source. Furthermore, amplification through cell-culture passaging can result in the selection and purification of variants normally present only at very low frequencies in the original host and can also give rise to lab-adapted viral strains not seen at all in the original patient. Therefore, there is the requirement to sequence viral genomes directly from the patient source material. This is challenging however, as low viral genome copy numbers preclude the use of randomly primed method in these scenarios due to an inherent lack of sensitivity, necessitating a targeted approached followed by PCR amplification of the virus in question. Amplification can be achieved in many ways, such as routine PCR, LAMP and other iso-thermal whole genome amplification reactions. Generally, these all require knowledge of the virus genome and require the ability to select pairs of nucleic acid oligo primers that anneal to the target genome.

The requirement for pairs of primers is a fundamental limitation however, as it presents strong constraints on where primers can be designed and increases sensitivity to changes in the underlying template, as is frequent in the case of virus evolution. Pairs of primers must be designed at a specific distance apart, adding constraints to the assay design and preventing the detection of structural rearrangements of the underlying genomic target—such as recombination events that give rise to deletions, insertion, defective genomes and subgenomic genomes. Such species are highly abundant in some viruses and can account for over 95% of the genetic material (such is the case with coronaviruses). To apply tiled approaches on multiple sequencing platforms, paired-primer approaches also necessitate the design and validation of alternative sets of primer-pairs spaced further apart in the genome to generate amplicons of different lengths as required per the specific platform (e.g. Illumina amplicons are 200-500 nts. Nanopore amplicons are ~2000-5000 nts).

Non-limiting examples of viral genomes for use of the present invention include: human immunodeficiency virus (HIV), herpes simplex virus (HSV-1 and HSV-2), human T-lymphotropic virus (HTLV), John Cunningham virus (JC Virus), vesicular stomatitis virus (VSV), hepatitis C virus (HCV), hepatitis B virus (HBV), Zika virus, Dengue virus, Chikungunya virus, Ebola virus, adeno-associated virus, aichi virus, Australian bat lyssavirus, BK polyomavirus, Banna virus, Barmah forest virus, Bunyamwera virus, Bunyavirus La Crosse, Bunyavirus snowshoe hare, Cercopithecine herpesvirus. Chandipura virus, Cosavirus A, Cowpox virus, Coxsackievirus, Crimean-Congo hemorrhagic fever virus, Dhori virus, Dugbe virus, Duvenhage virus, Eastern equine encephalitis virus. Echovirus, Encephalomyocarditis virus, Epstein-Barr virus, European bat lyssavirus, Hepatitis G virus, Hantaan virus, Hendra virus, Hepatitis A virus, Hepatitis E virus, Hepatitis delta virus, Horsepox virus, human adenovirus, human astrovirus, human coronavirus, human cytomegalovirus, human enterovirus 68, human enterovirus 70, human herpesvirus 6, human herpesvirus 7, human herpes virus 8, human metapneumovirus, human papillomavirus (HPV) 1, HPV 2, HPV 16, HPV 18, human parainfluenza, human parvovirus B19, human respiratory syncytial virus, human rhinovirus, human severe acute respiratory syndrome (SARS) coronavirus (SARS-CoV-1, MERS, SARS-CoV-2 and variants thereof), human spumaretrovirus, human torovirus, influenza A virus, influenza B virus, influenza C virus, Isfahan virus, JC polyomavirus, Japanese encephalitis virus, Junin arenavirus, KI polyomavirus, Kunjin virus, Lagos bat virus, Lake Victoria marburgvirus, Langat virus, Lassa virus, Lordsdale virus, Louping ill virus, lymphocytic choriomeningitis virus. Machupo virus, Mayaro virus, Middle East Respiratory Syndrome (MERS) coronavirus, measles virus, Mengo encephalomyocarditis virus, Merkel cell polyomavirus, Mokola virus, Molluscum contagiosum virus, monkeypox virus, mumps virus, Murray valley encephalitis virus, New York virus, Nipah virus, Norwalk virus, O'nyong-nyong virus, Orf virus, Oropouche virus, parainfluenza virus, Pichinde virus, Poliovirus, Punta toro phlebovirus, Puumala virus, Rabies virus, Respiratory Syncytial Virus, Rift valley fever virus, Rosavirus A, Ross river virus, Rotavirus A, Rotavirus B, Rotavirus C, Rubella virus, Sagiyama virus, Salivirus A, sandfly fever Sicilian virus, Sapporo virus, Semliki forest virus, Seoul virus, simian foamy virus, simian virus 5, Sindbis virus, Southhampton virus, St. Louis encephalitis virus, tick-borne powassan virus, torque teno virus, Toscana virus, Ulukuniemi virus, vaccinia virus, varicella-zoster virus, variola virus, Venezuelan equine encephalitis virus, vesicular stomatitis virus, western equine encephalitis virus, WU polyomavirus, West Nile virus, Yaba monkey tumor virus, Yaba-like disease virus, and yellow fever virus.

The present inventors designed a novel method for a tiled targeted whole genome sequencing assay based upon the ClickSeq method for NGS that overcome the limitations of applying a pair-primer approach, U.S. Patent No. 20190256547, relevant portions incorporated herein by reference. Rather than using multiple primer-pairs, ClickSeq only requires one template-specific primer per amplicon. A unique feature of ClickSeq is that the 3'end of an amplified cDNA segment is generated stochastically through the use of terminating 3' azido nucleotides that are incorporated during reverse transcription. Therefore, a second downstream primer is click-ligated onto the cDNA and so a template-specific primer is not required.

Example 1. Whole Genome Sequencing of a Virus Isolate

To achieve whole genome sequencing of a virus isolate, the inventors used multiple tiled primers spaced evenly along the virus genome, each only targeting one annealing site and without the need to design corresponding paired PCR primers. This simplifies the assay design, but importantly removes that constraint and limitations ordinary imposed, as described above. The method was used to accurately capture full-length viral genomes as well as the recombination RNA species present (such as sub-genomic mRNAs). To the inventors' knowledge, this is only such single-primer tiled sequencing approach described to date. With this approach, the same validated primer set can be used for any platform, regardless of the length of fragments that are required for sequencing. The inventors can also adjust the 3'azido:3'deoxynucleotide mix ratio by diluting the nucleotide mix with dNTPs in order to generate amplicons of increased lengths. This greatly improves flexibility of the pipeline and obviates the need to redesign tiled primers per platform.

Figure 1B:
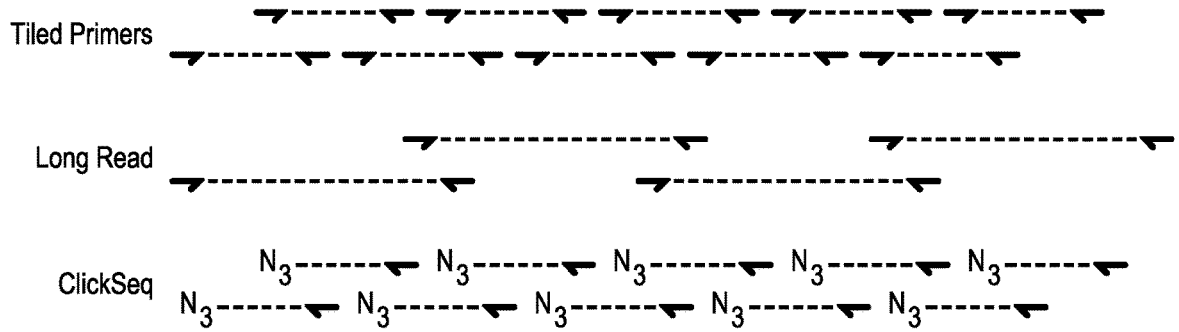
Figure 1C:
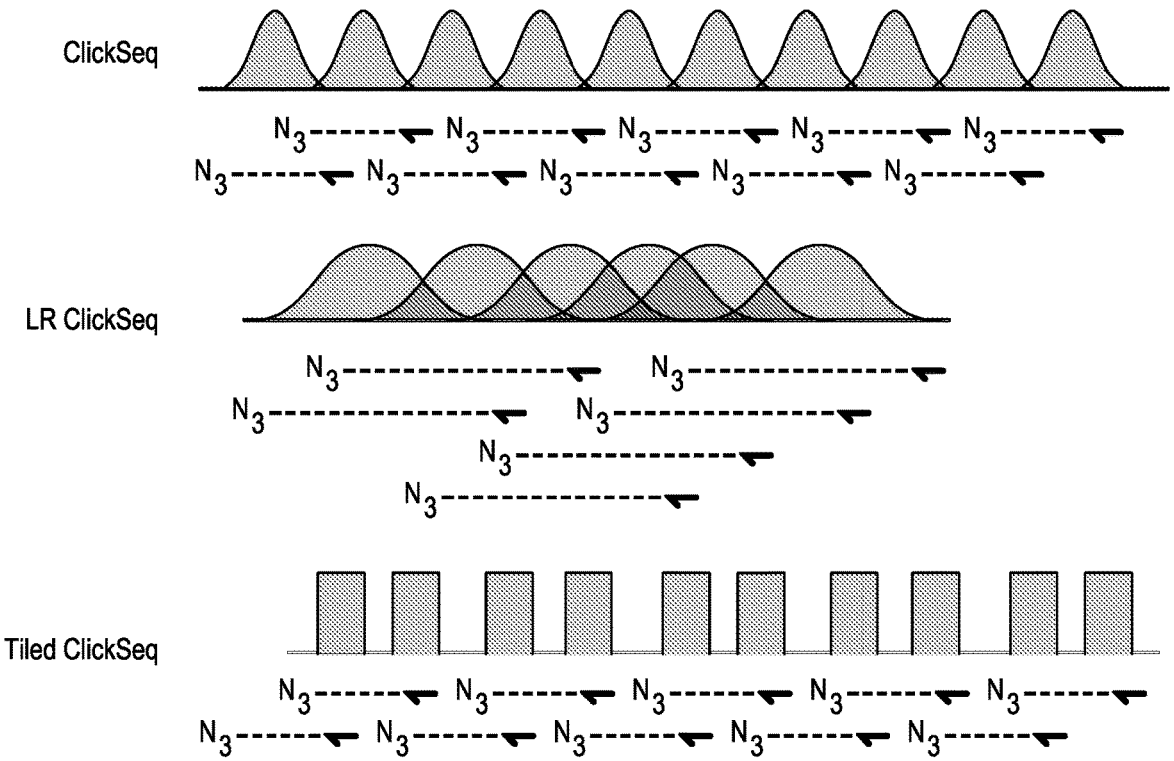

FIGS. 1A to 1C show a schematic of tiled approaches for whole genome sequencing (WGS) of target virus. FIG. 1A) Coronavirus genome is a single-stranded positive sense RNA genome with a poly(A)-tail. Multiple sub-genomic mRNAs are generated through discontinuous replication and can account for the majority of virus genetic material. FIG. 1B shows that tiled approaches for whole virus genome sequencing require carefully designed compatible pairs of forward (left) and reverse (right) primers. For long reads, new pairs must be designed. In tiled ClickSeq, only one templated primer is required, with the left end generated through stochastic termination of the reverse transcription reaction. FIG. 1C shows the predicted read coverage of ClickSeq data over the virus genome is illustrated for short and long reads (LR) for the left hand read derived from the azido (N3) end or for the right hand read derived from the tiled primer.

The inventors designed tiled primers cognate to the deposited SARS-CoV2 genome (accession number: MN985325) using the primalseq webserver (http://primal.zibraproject.org/#) with an amplicon distance of approximately 500 nt between each primer pair. The inventors used only the 'right' primer sequences generated by primalseq and append the Illumina p7 adaptor to these (e.g. GTGACTGGAGTTCAGACGTGTGCTCTTCCGATCT (SEQ ID NO:1)+TGTCTCACCACTACGACCGTAC (SEQ ID NO:2). Primers were ordered from IDT in plate format. Each primer was then pooled in equimolar ratios to yield a SARS-CoV2 specific primer-i7 pool used for the RT step of tiled-ClickSeq.

The inventors obtained 200 ng of extracted RNA from SARS-CoV2 isolates deposited at the World Reference Center for Emerging Viruses and Arboviruses (WRECEVA) at UTMB. The inventors performed two ClickSeq library preparations in parallel: random-primed ClickSeq (6N-CS) and Tiled-ClickSeq (T-CS). All subsequent Tiled-ClickSeq reactions were performed using the canonical ClickSeq protocols. Tiled-ClickSeq synthesis generated robust libraries (see FIG. 2).

Figure 2:
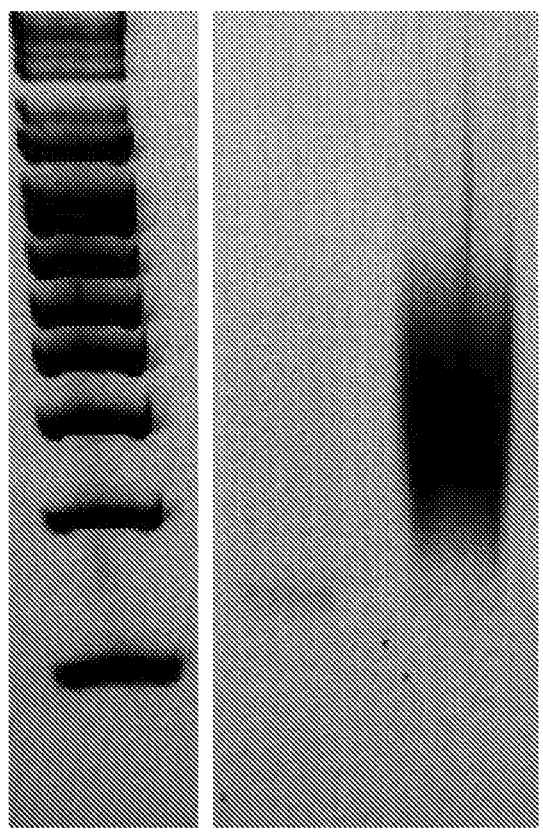
FIG. 2 is an agarose gel of final NGS library showing robust Tiled-ClickSeq library synthesis with SARS-CoV2 as input (right lane) but not for off-target SHC coronavirus (left lane). Even fragment distribution was obtained at expected size range at 200-600 bp.

FIG. 2 shows an agarose gel of final NGS library using robust Tiled-ClickSeq library synthesis with SARS-CoV2 as input (right lane) but not for off-target SHC014-CoV bat coronavirus (left lane). Even fragment distribution was obtained at expected size range at 200-600 bp. Final libraries were sequenced at the UTMB Next-Generation Sequencing core using a 300-cycle low-volume flowcell of an Illumina MiniSeq (yields ~8M 2×150 reads).

Illumina reads were mapped to the virus genome using HISAT2. For the random primed ClickSeq dataset, the inventors obtained 23.1 million reads, of which 4.6M (19.9%) mapped to the virus reference genome. For the Tiled-ClickSeq dataset, 712K reads were obtained, of which 700K (98.4%) mapped to the reference genome. Therefore, the Tiled-ClickSeq approach substantially improved specificity of the output genome to the targeted virus. Mapped reads were de-duplicated using unique molecular identifiers (UMIs) nested in the ClickSeq click-adaptor, leaving 599'814 unique mapped reads and complete genome coverage from nucleotide 3 to 29851 (22nts from the 3' end of the genome) was obtained. A saw-tooth pattern of read coverage over the genome was generated (FIGS. 3A and 3B) with 'teeth' appearing as expected just upstream of each designed tiled primer. Peaks of coverage for each 'tooth' ranged from ~13000× to ~1000×. Lowest coverage was 32 reads, which is nonetheless sufficient to confidently reconstruct a consensus genetic sequence from nucleotides 3 to 29851. Using the present invention, the inventors were able to correct two single nucleotide variants from the reference sequence: A28144C and C18060T.

Figure 3A:
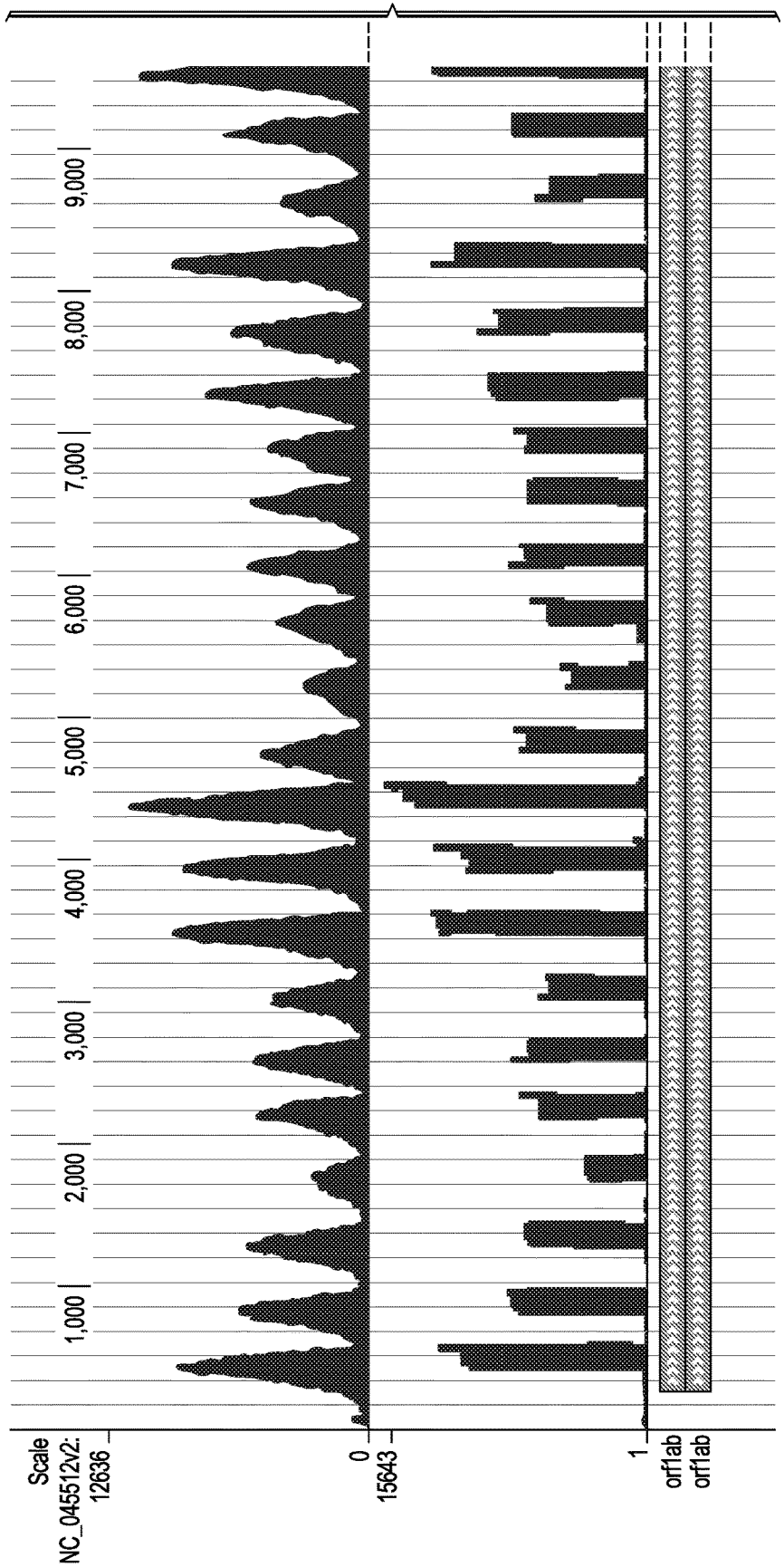
FIGS. 3A and 3B show data illustrating coverage over SARS-CoV2 (TVP Washington isolate obtained from UTMB WRECEVA) genome using the Tiled-ClickSeq approach sequenced using an Illumina NextSeq. Total genome coverage is achieved. 'Saw-tooth' pattern indicates distributed fragments generated per tiled primer as is a unique characteristic of ClickSeq due to stochastic termination of cDNA synthesis during reverse transcription.
Figure 3A:
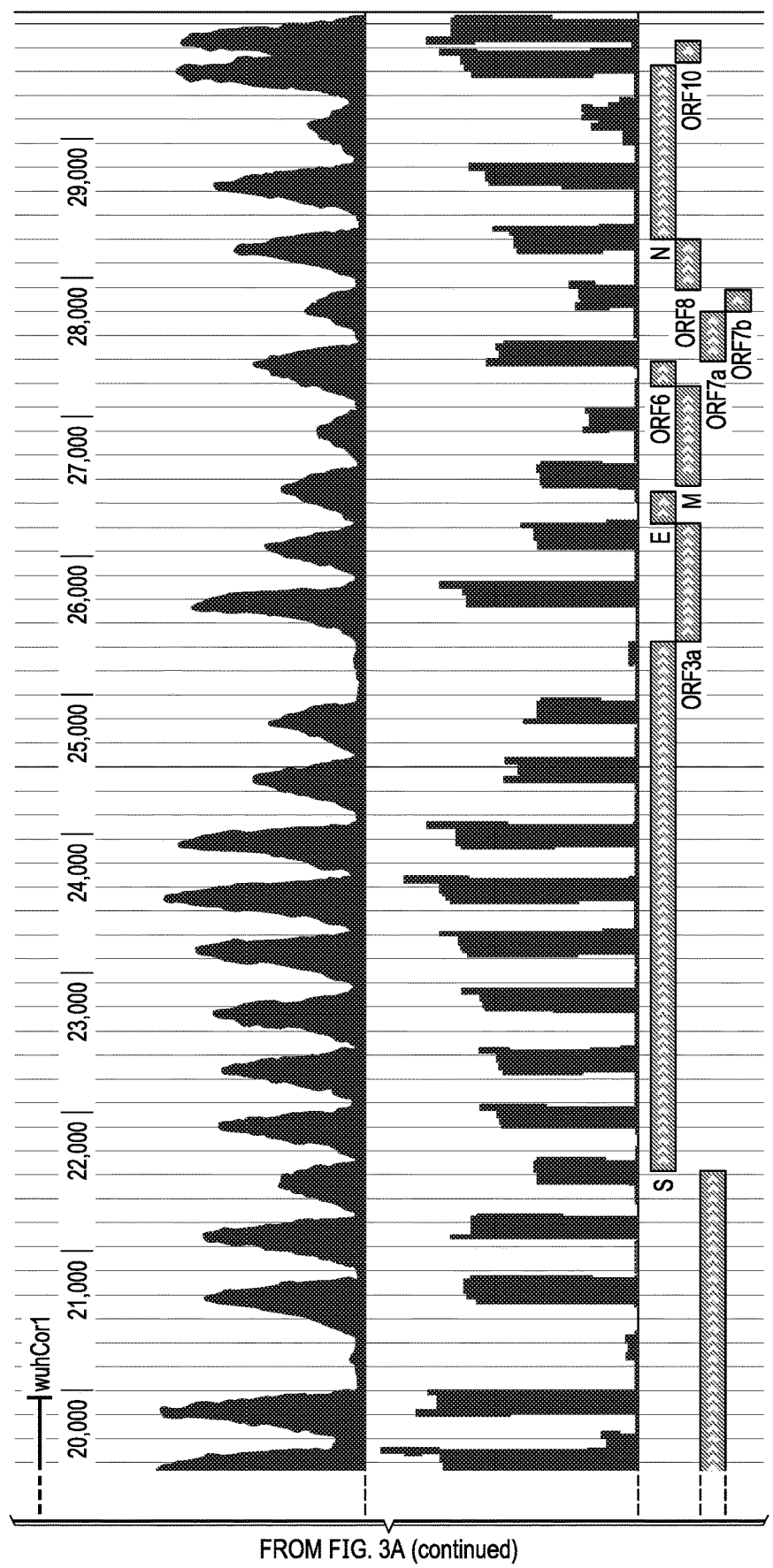
Figure 3B:
Figure 3B:
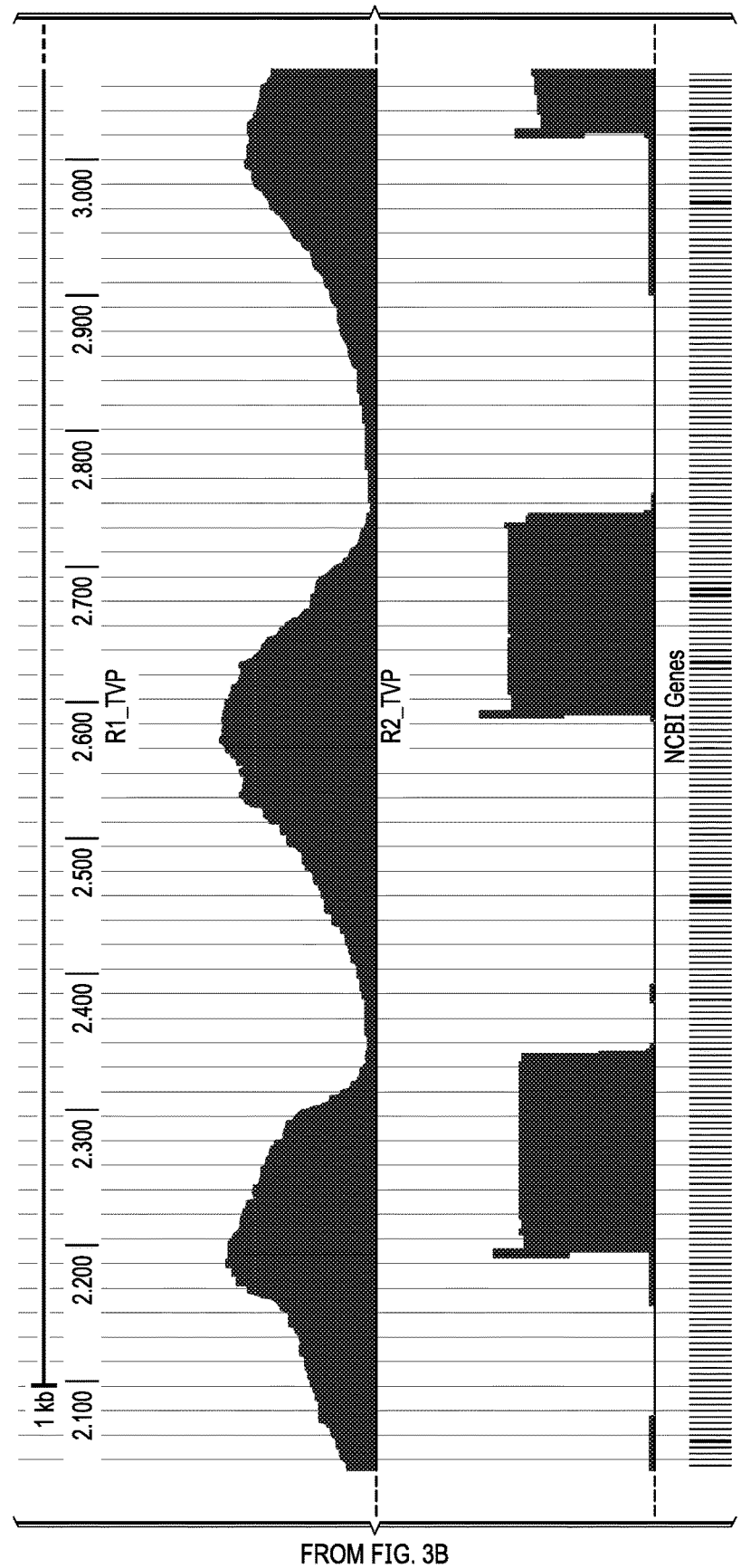
Figure 3B:
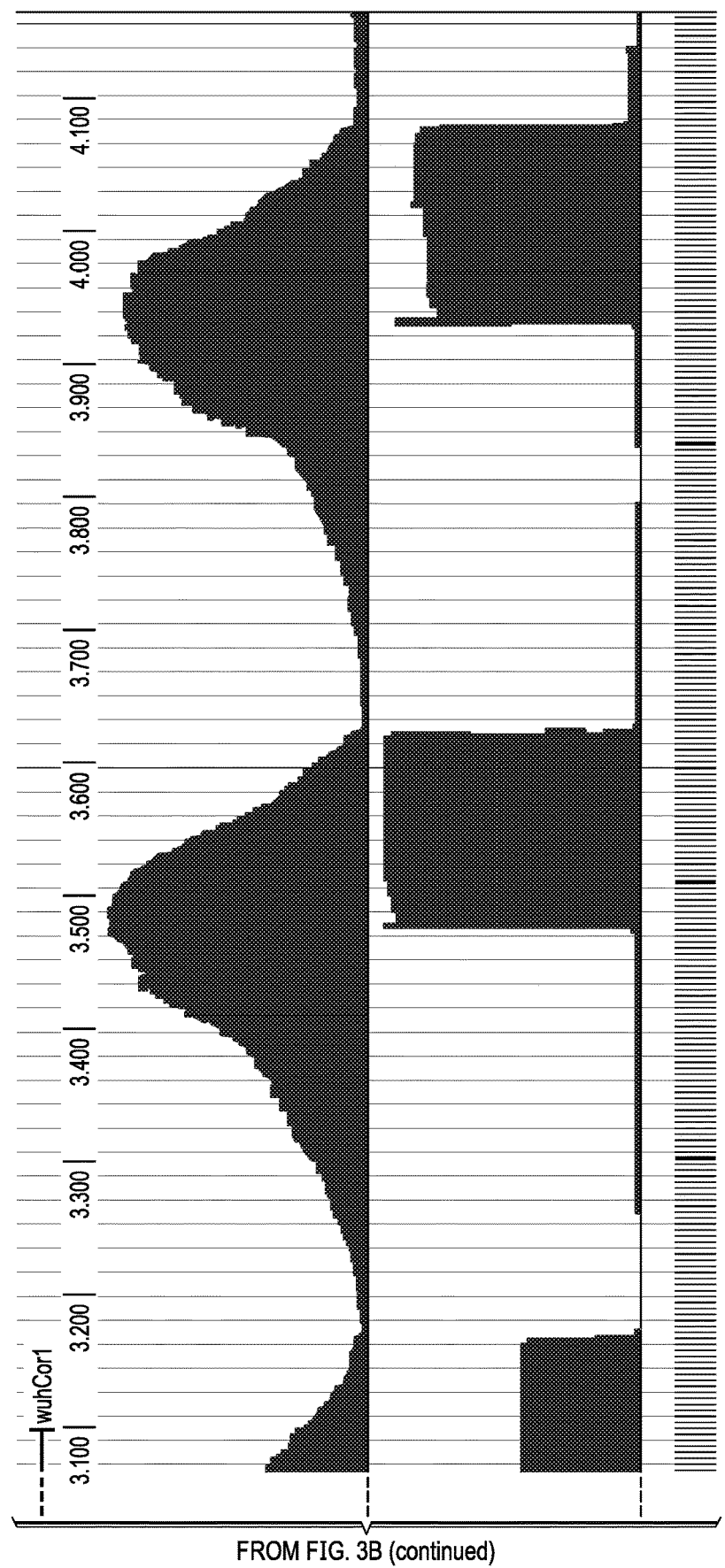

FIGS. 3A and 3B show data illustrating coverage over SARS-CoV2 (TVP23153 Washington isolate obtained from UTMB WRECEVA) genome using the Tiled-ClickSeq approach sequenced on an Illumina NextSeq550. Total genome coverage is achieved. 'Saw-tooth' pattern indicates distributed fragments generated per tiled primer as is a unique characteristic of ClickSeq due to stochastic termination of cDNA synthesis during reverse transcription.

The inventors repeated the Tiled-ClickSeq library, except using a larger ratio of dNTPs to AzNTPs in the reverse transcription step of the canonical ClickSeq protocol in order to obtain longer cDNA fragments. Similarly to above, a cDNA library was successfully obtained and the inventors gel purified cDNA fragments larger than 700 bp. This larger library was used as input for an Oxford Nanopore Technologies Sequencing by Ligation Library prep kit (SQK-LSK109) to append the required adaptors and motor proteins for nanopore sequencing.

Nanopore reads were adaptor-trimmed using Porechop, filtered to retain only reads greater than 1000 bp in length and mapped to the virus genome using hwa. This yielded 317'903 processed reads, of which 317'736 (99.9%) mapped to the target virus and returned complete genome coverage from nucleotide 1 to 29903 (complete genome coverage). A saw-tooth pattern of read coverage over the genome was generated (FIGS. 3C and 3D) with 'teeth' appearing as expected just upstream of each designed tiled primer. Peaks of coverage for each 'tooth' ranged from ~24000× to ~4000×. Lowest coverage was 13 reads at the very 5' end of the genome. Excluding the 5'UTR, the lowest coverage was 1784×. Using the present invention, similarly to the illumina data, inventors were able to correct two single nucleotide variants from the reference sequence: A28144C and C18060T.

Figure 3C:
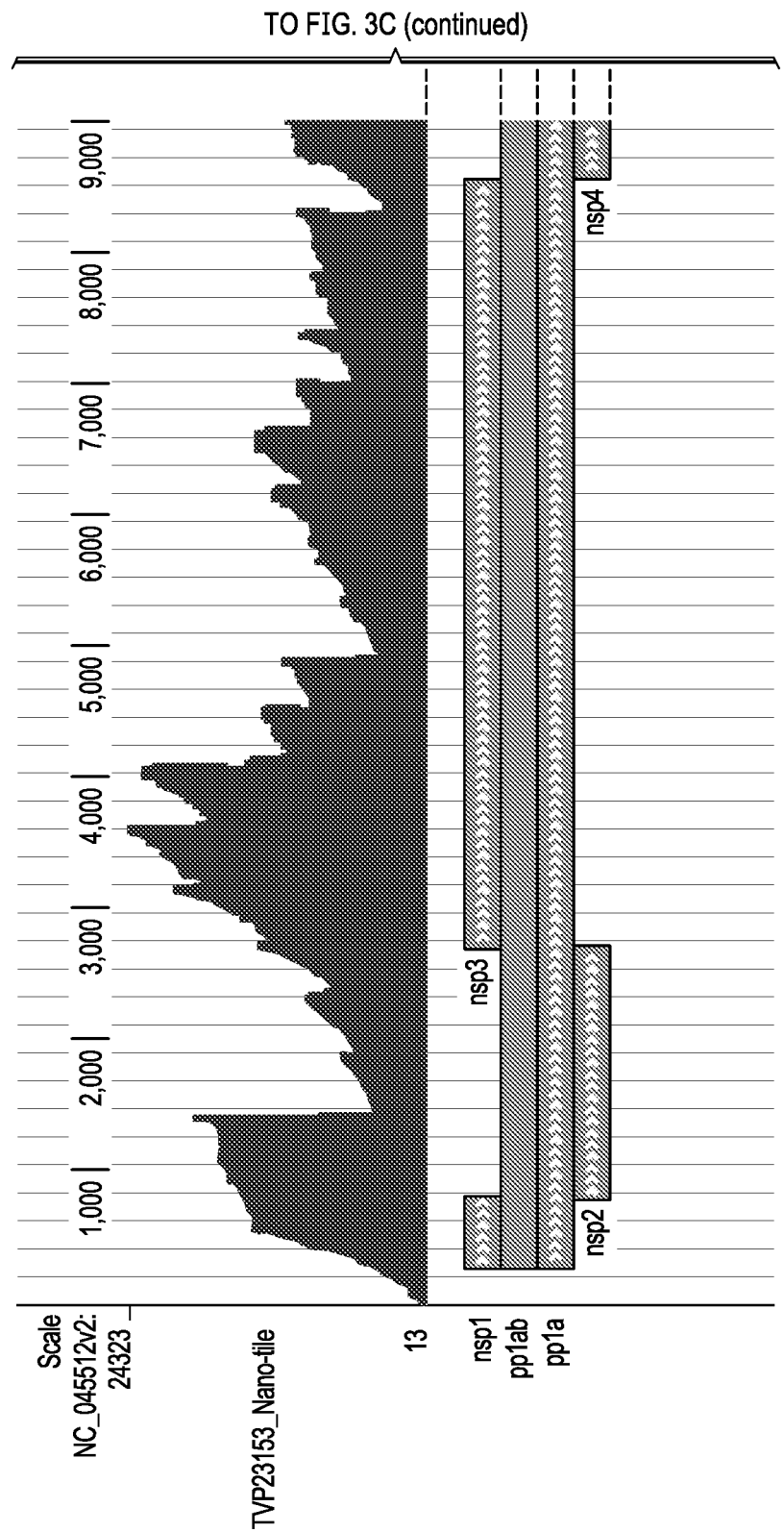
FIGS. 3C and 3D show data illustrating coverage over SARS-CoV2 (TVP Washington isolate obtained from UTMB WRECEVA) genome using the Tiled-ClickSeq approach sequenced using an Oxford Nanopore Technologies's MinION device. Total genome coverage is achieved. 'Saw-tooth' pattern indicates distributed fragments generated per tiled primer as is a unique characteristic of ClickSeq due to stochastic termination of cDNA synthesis during reverse transcription.
Figure 3C:
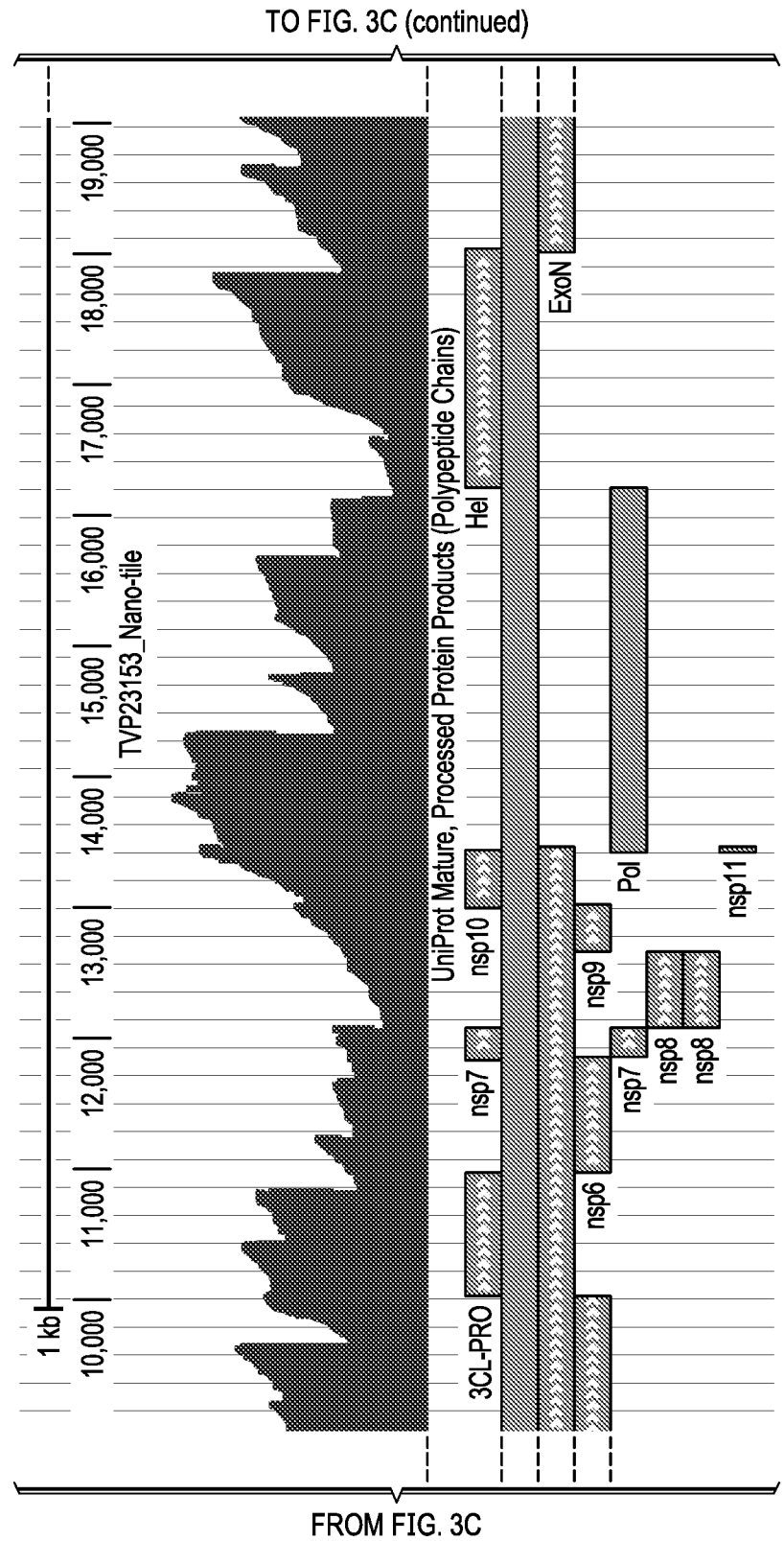
Figure 3C:
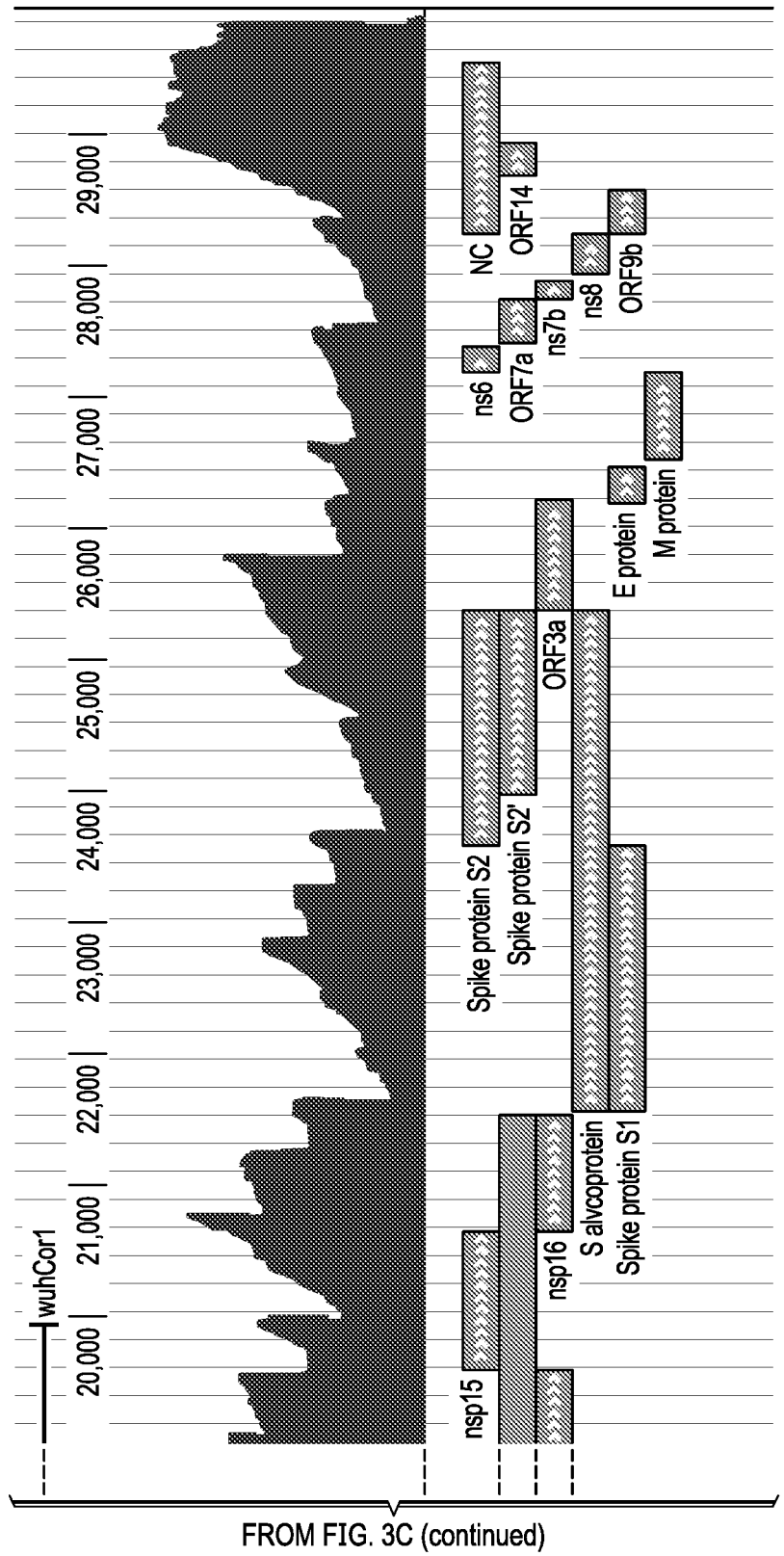
Figure 3D:
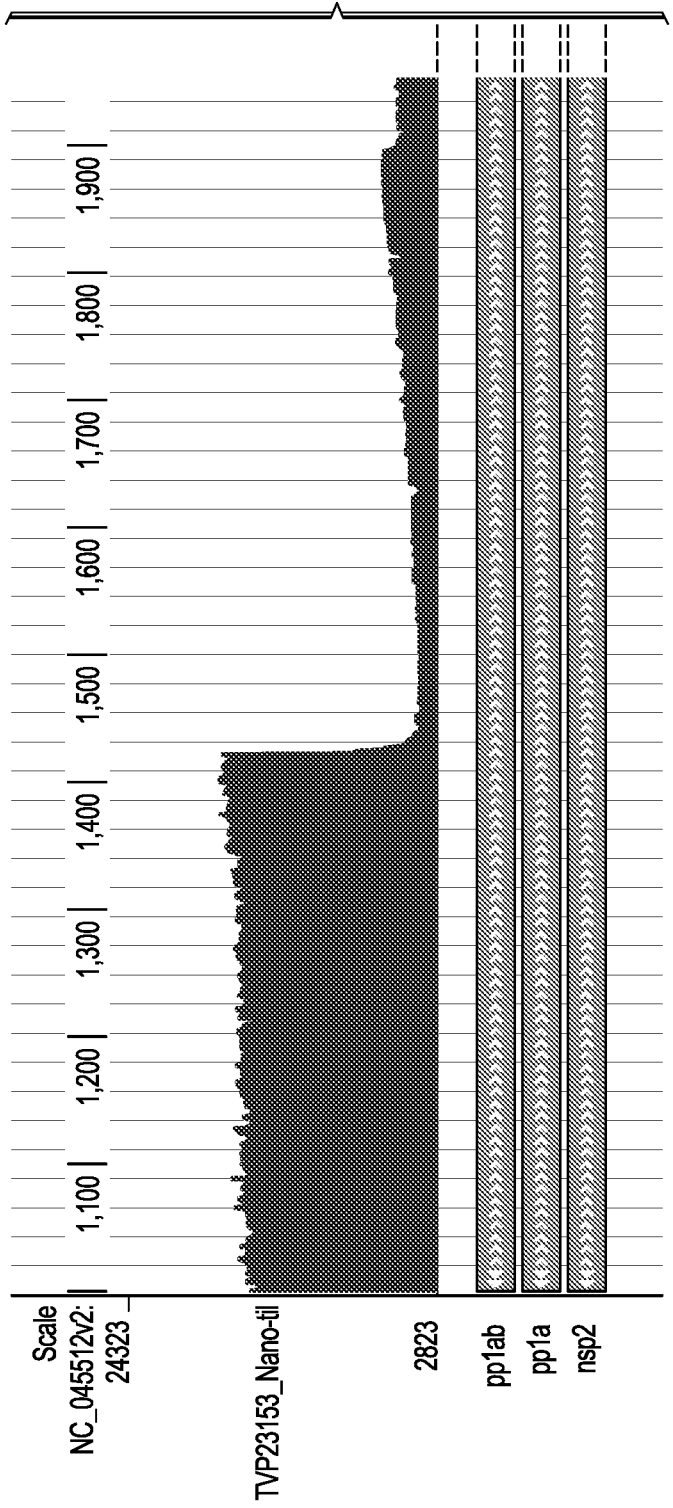
Figure 3D:
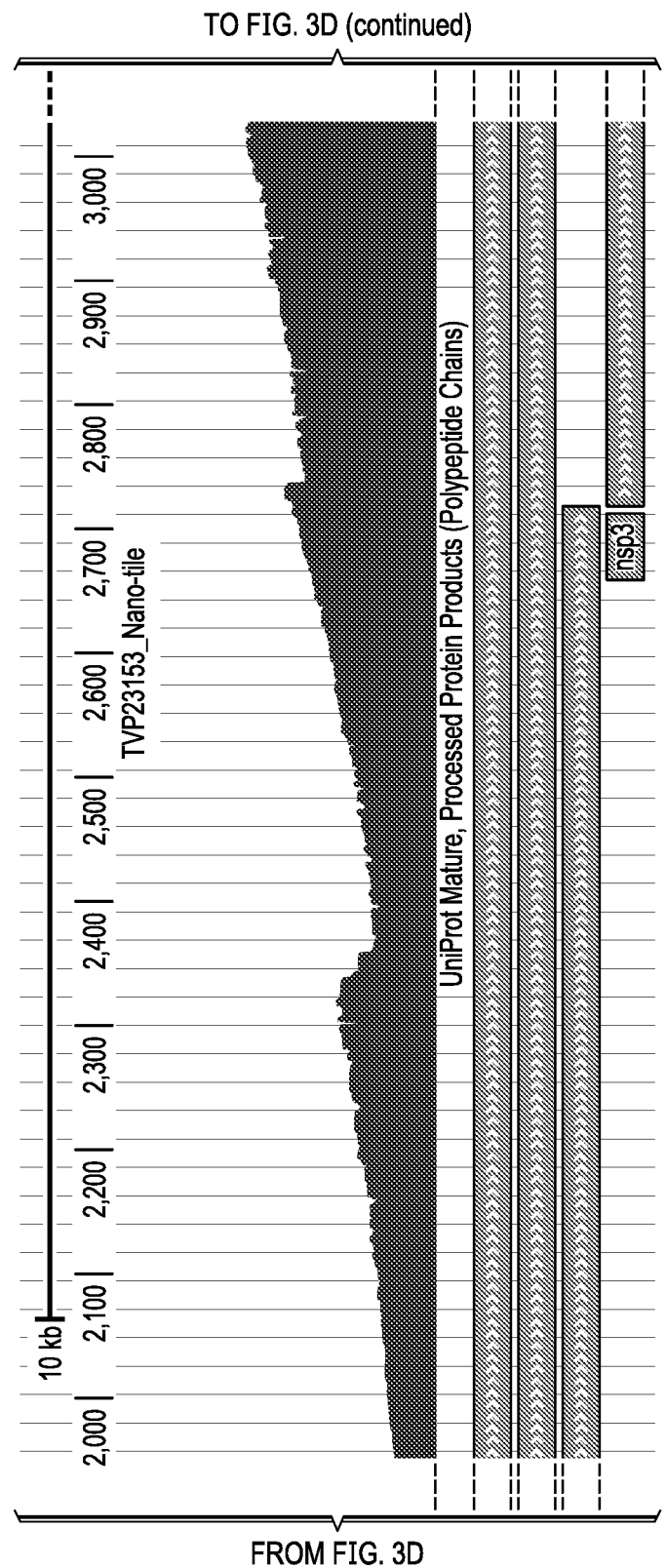
Figure 3D:
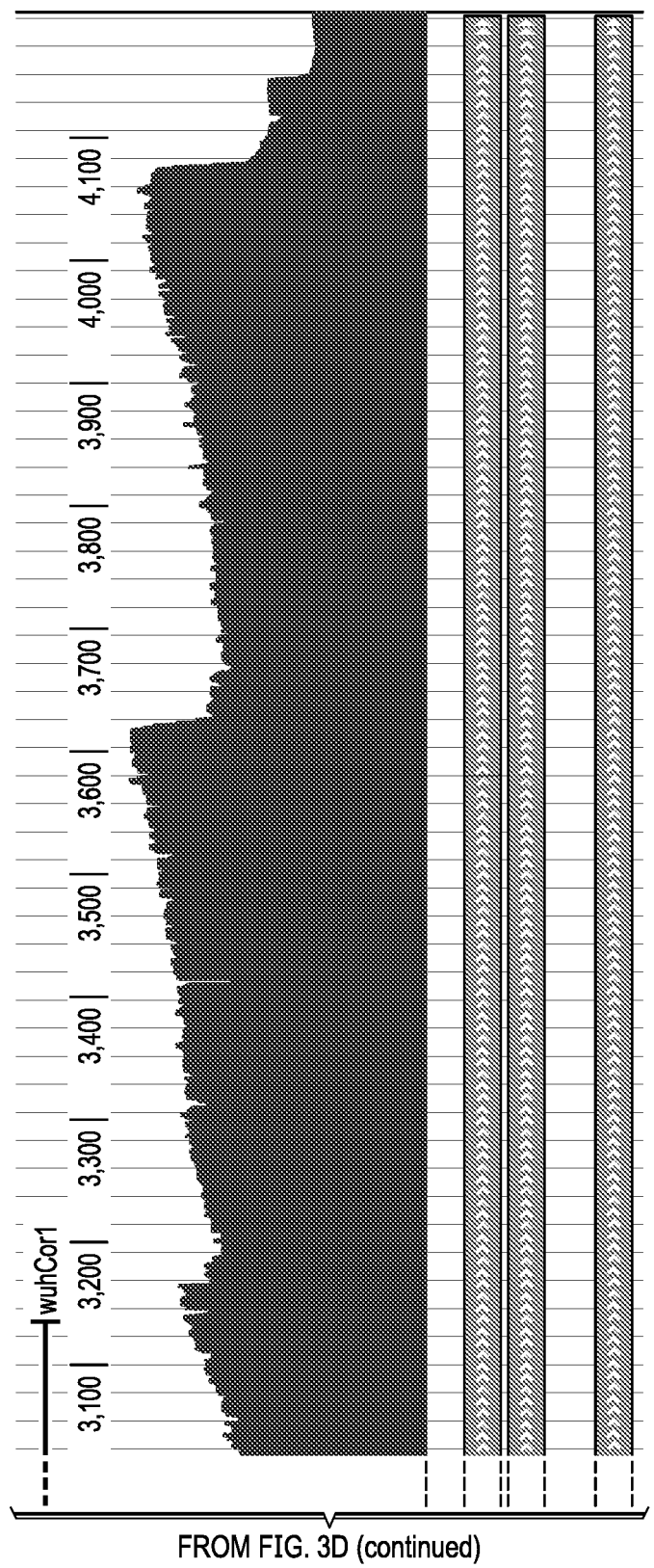

FIGS. 3C and 3D show data illustrating coverage over SARS-CoV2 (TVP23153 Washington isolate obtained from UTMB WRECEVA) genome using the Tiled-ClickSeq approach sequenced using a Oxford Nanopore Technologies's MinION device. Again, total genome coverage is achieved. 'Saw-tooth' pattern indicates distributed fragments generated per tiled primer as is a unique characteristic of ClickSeq due to stochastic termination of cDNA synthesis during reverse transcription.

An important aspect of the present invention is in the use of pair-end sequencing. As the left hand read of every paired sequence reads originates from the 3' azido-termination site, it is randomly distributed. However, the right hand read is derived from the primer binding site, and as such will align in the very region at which that primer was cognate. Therefore, with paired-end sequencing, the inventors were able to deduce the tiled primer that gave rise to the left hand read. This is important, as it allows the user to trim away any nucleotides in these left hand reads that may have derived from the original primer. Such primer-derived nucleotides might aberrantly report an incorrect nucleotide resulting in the failure to detect SNVs in these regions. This may be especially important when the tiled reads exhibit extensive overlapping of the individual 'teeth'.

A further important aspect of the present invention is in the detection of genomic rearrangements that arise due to RNA recombination. RNA recombination is especially important in coronaviruses as it is responsible for the formation of the sub-genomic mRNAs (sgmRNAs) which can account for >90% of the total genetic material sequenced and defective RNAs (D-RNAs). Due to the stochastic and unpredictable nature of RNA recombination in RNA viruses, RNA recombination events would generate a range of unexpected amplicon sizes. This complicates paired-primer approaches as pairs cannot be designed without prior knowledge of the recombination event (which is unknown prior to sequencing). Therefore, RNA recombination events can only be captured in a highly multiplexed PCR if non-paired primers happened by chance to flank the recombination junction. In a Tiled-ClickSeq approach, by using only one-template specific primer, the inventors removed the need for a cognate downstream primer, and therefore successfully generated cDNA fragments of the desired lengths regardless of the nature of the template upstream of the primer binding site. As a result, the method agnostically captures all known and unknown recombination events. In this dataset, the inventors were able to robustly detect multiple sgmRNAs as well as co-circulating structural variants (Table 1). All of these same events were discovered in the random-primed ClickSeq library made of the same material, validating their correct assignment and detection.

TABLE 1

Top ten detected recombination events annotated using the ViReMa software package. Events are reported in BED format:

| Reference | From | To | Result | Count | Strand | Interpretation |
|---|---|---|---|---|---|---|
| NC_045512.2 | 71 | 27390 | Deletion | 254 | + | sgmRNA - ORF7a |
| NC_045512.2 | 70 | 26474 | Deletion | 194 | + | sgmRNA - novel ORF |
| NC_045512.2 | 70 | 28261 | Deletion | 88 | + | sgmRNA - ORF N |
| NC_045512.2 | 70 | 21557 | Deletion | 50 | + | sgmRNAs - ORF Spike |
| NC_045512.2 Spike | 23554 | 23583 | Deletion | 33 | + | Structural Variant, |
| NC_045512.2 | 516 | 523 | Deletion | 13 | + | Structural Variant, Nsp1 |
| NC_045512.2 | 510 | 525 | Deletion | 12 | + | Structural Variant, Nsp1 |
| NC_045512.2 | 508 | 524 | Deletion | 9 | + | Structural Variant, Nsp1 |
| NC_045512.2 | 509 | 519 | Deletion | 8 | + | Structural Variant, Nsp1 |
| NC_045512.2 | 26786 | 26821 | Deletion | 6 | + | Structural Variant, M |

To demonstrate the utility of the present invention for convenient whole genome sequencing of virus isolates, the inventors obtained 12 coronavirus RNA samples from the WRECEVA center and synthesized random-primed ClickSeq and Tiled-ClickSeq libraries in parallel for each sample. For the Tiled-ClickSeq libraries, cDNA libraries of specific sizes were purified from cut agarose gels yielding fragment sizes of 200-600 bp suitable for Illumina sequencing and >600 bp suitable for Nanopore sequencing. The Illumina libraries were multiplexed and sequenced at the UTMB Next-Generation Sequencing core obtaining >3M raw paired-end reads per sample (2×150 bp). The Nanopore libraries were barcoded using the Oxford Nanopore Technologies's Native Barcoding kit (NBD104) followed by sequencing by ligation (SQK-LSK 109) following the manufacturer's protocol. Multiplexed libraries were sequencing on a single MinION flowcell yielding >260K reads per sample.

Reference genomes were reconstructed for all samples from both the Illumina and the Nanopore Tiled-ClickSeq data using Pilon. Between 6 and 16 Single Nucleotide Variants (SNVs) were resolved for each samples relative to the input reference sequence (Accession: NC_045512.2). Importantly, the Tiled-ClickSeq libraries yielded the exact same SNVs for each of the 12 samples regardless of whether they were sequenced by Illumina or Nanopore (Table 2), with the exception of one sample (CoV #9). Further scrutiny revealed that this SNV (C14220T) was a minority variant present in approximately 50% of all the mapped viral reads. Furthermore, the random-primed ClickSeq methods also yielded the same SNVs in each sample with the exception of CoV samples 2, 9, and 12, that failed to identify one or two SNVs per sample.

TABLE 2

Single Nucleotide Variants (SNVs) identified by Tiled-ClickSeq (Illumina and Nanopore sequencing) and by random-primed ClickSeq for 12 SARS-CoV-2 isolates obtained from the WRECEVA, UTMB. SNVs were identified using Pilon using default settings.

| | Random ClickSeq SNVs (Illumina) | Tiled ClickSeq SNVs (Illumina) | Tiled ClickSeq SNVs (Nanopore) |
|---|---|---|---|
| CoV#1 | C241T | C241T | C241T |
| | C1059T | C1059T | C1059T |
| | C3037T | C3037T | C3037T |
| | G3068A | G3068A | G3068A |
| | C9169T | C9169T | C9169T |
| | C14408T | C14408T | C14408T |
| | A23403G | A23403G | A23403G |
| | G25563T | G25563T | G25563T |
| CoV#2 | C3037T | T168C | T168C |
| | C14408T | C241T | C241T |
| | A23403G | C3037T | C3037T |
| | C24797T | C14408T | C14408T |
| | | A23403G | A23403G |
| | | C24797T | C24797T |
| CoV#3 | C241T | C241T | C241T |
| | C1059T | C1059T | C1059T |
| | C3037T | C3037T | C3037T |
| | C14408T | C14408T | C14408T |
| | A23403G | A23403G | A23403G |
| | G25563T | G25563T | G25563T |
| CoV#4 | C241T | C241T | C241T |
| | C1059T | C1059T | C1059T |
| | C3037T | C3037T | C3037T |
| | C14408T | C14408T | C14408T |
| | A18082G | A18082G | A18082G |
| | A23403G | A23403G | A23403G |
| | G25563T | G25563T | G25563T |
| | A27357G | A27357G | A27357G |
| | C27964T | C27964T | C27964T |
| CoV#5 | C241T | C241T | C241T |
| | C1059T | C1059T | C1059T |
| | C3037T | C3037T | C3037T |
| | C10319T | C10319T | C10319T |
| | C14408T | C14408T | C14408T |
| | A23403G | A23403G | A23403G |
| | G25563T | G25563T | G25563T |
| | C27964T | C27964T | C27964T |
| | C28531T | C28531T | C28531T |
| CoV#6 | T490A | T490A | T490A |
| | C3177T | C3177T | C3177T |
| | C6040T | C6040T | C6040T |
| | C6843T | C6843T | C6843T |
| | C8782T | C8782T | C8782T |
| | C8950T | C8950T | C8950T |
| | G12478A | G12478A | G12478A |
| | T18736C | T18736C | T18736C |
| | C24034T | C24034T | C24034T |
| | T26729C | T26729C | T26729C |
| | C26801T | C26801T | C26801T |
| | G28077C | G28077C | G28077C |
| | T28144C | T28144C | T28144C |
| | C28896G | C28896G | C28896G |
| | C29451T | C29451T | C29451T |
| | A29700G | A29700G | A29700G |
| CoV#7 | C241T | C241T | C241T |
| | C3037T | C3037T | C3037T |
| | C8664T | C8664T | C8664T |
| | C14408T | C14408T | C14408T |
| | C15026T | C15026T | C15026T |
| | T15264C | T15264C | T15264C |
| | A23403G | A23403G | A23403G |
| | C27575T | C27575T | C27575T |
| CoV#8 | C241T | C241T | C241T |
| | C1059T | C1059T | C1059T |
| | C3037T | C3037T | C3037T |
| | C14408T | C14408T | C14408T |
| | A23403G | A23403G | A23403G |
| | G25563T | G25563T | G25563T |
| CoV#9 | C1059T | C241T | C241T |
| | C3037T | C1059T | C1059T |
| | C14408T | C3037T | C3037T |
| | A23403G | C14408T | C14220T |
| | G25563T | A23403G | C14408T |
| | | G25563T | A23403G |
| | | | G25563T |
| CoV#10 | T168C | T168C | T168C |
| | C241T | C241T | C241T |
| | C3037T | C3037T | C3037T |
| | C14408T | C14408T | C14408T |
| | A23403G | A23403G | A23403G |
| | C24797T | C24797T | C24797T |
| CoV#11 | A3003T | A3003T | A3003T |
| | C8782T | C8782T | C8782T |
| | C10811T | C10811T | C10811T |
| | T10813A | T10813A | T10813A |
| | C17747T | C17747T | C17747T |
| | A17858G | A17858G | A17858G |
| | C18060T | C18060T | C18060T |
| | A24694T | A24694T | A24694T |
| | T28144C | T28144C | T28144C |
| CoV#12 | C1059T | C241T | C241T |
| | C3037T | C1059T | C1059T |
| | T10213C | C3037T | C3037T |
| | C10319T | T10213C | T10213C |
| | C14408T | C10319T | C10319T |
| | T17137C | C14408T | C14408T |
| | A23403G | T17137C | T17137C |
| | G25563T | A23403G | A23403G |
| | C27964T | G25563T | G25563T |
| | | C27964T | C27964T |

Example 2. Tiled-ClickSeq for Targeted Sequencing of Complete Coronavirus Genomes with Simultaneous Capture of RNA Recombination and Minority Variants High-throughput genomics of SARS-CoV-2 is essential to characterize virus evolution and to identify adaptations that affect pathogenicity or transmission. While single-nucleotide variations (SNVs) are commonly considered as driving virus adaption, RNA recombination events that delete or insert nucleic acid sequences are also critical. Whole genome targeting sequencing of SARS-CoV-2 is typically achieved using pairs of primers to generate cDNA amplicons suitable for Next-Generation Sequencing (NGS). However, paired-primer approaches impose constraints on where primers can be designed, how many amplicons are synthesized and requires multiple PCR reactions with non-overlapping primer pools. This imparts sensitivity to underlying SNVs and fails to resolve RNA recombination junctions that are not flanked by primer pairs. To address these limitations, the inventors have designed an approach called 'Tiled-ClickSeq'. Tiled-ClickSeq uses hundreds of tiled-primers spaced evenly along the virus genome in a single reverse-transcription reaction. The other end of the cDNA amplicon is generated by azido-nucleotides that stochastically terminate cDNA synthesis, obviating the need for a paired-primer. A sequencing adaptor containing a Unique Molecular Identifier (UMI) is appended using click-chemistry and a PCR reaction using Illumina adaptors generates a final NGS library. Tiled-ClickSeq provides complete genome coverage, including the 5'UTR, at high depth and specificity to virus on both Illumina and Nanopore NGS platforms. Here, the inventors used the present invention to analyze multiple SARS-CoV-2 isolates and simultaneously characterize minority variants, sub-genomic mRNAs (sgmRNAs), structural variants (SVs) and D-RNAs. It is shown herein that Tiled-ClickSeq provides a convenient and robust platform for SARS-CoV-2 genomics that captures the full range of RNA species in a single, simple assay.

Virus genomics and Next-Generation Sequencing (NGS) are an essential component of viral outbreak responses (1). Reconstruction of consensus genetic sequences is essential to identify adaptations correlated with changes in pathogenicity or transmission (2). In addition to single nucleotide variations, studies of SARS-CoV-2 have identified numerous genomic structural variants (SVs) (3) that arise due to non-homologous RNA recombination. SVs typically comprise small insertions/deletions that nonetheless allow the variant genome to independently replicate and transmit. Numerous SVs have been described for CoVs including deletions of the accessory open reading frames (aORFs) (4, 5) and changes in spike protein observed in the B.1.1.7 and other variants of concern (6). Adaptation of SARS-CoV-2 also occurs during passaging in cell-culture, such as small deletions that arise near the furin cleavage site of spike protein during amplification on Vero cells (7). These deletions can alter the fitness and virulence of SARS-CoV-2 isolates and thus must be genetically characterized prior to passaged stock use in subsequent studies.

Similar to SVs, non-homologous RNA recombination also gives rise to Defective-RNAs (D-RNAs), also known as Defective Viral Genomes (DVGs). D-RNAs have been observed in multiple studies of coronaviruses (CoVs), including mouse hepatitis virus (MHV) (8-11), bovine CoV (12), avian infectious bronchitis virus (IBV) (13), human CoV 299E (14-17). As shown in Example 1, it is demonstrated that SARS-CoV-2 is >10-fold more recombinogenic in cell culture than other CoVs such as MERS (18) and generates abundant D-RNAs containing RNA recombination junctions that most commonly flank U-rich RNA sequences. D-RNAs may change the fitness, disease outcomes and vaccine effectiveness for SARS-CoV-2 similar to other respiratory pathogens such as influenza and RSV (19). Together, these findings highlight the need to identify these RNA changes and their impact on SARS-CoV-2 infection and pathogenesis. Whole genome sequencing can be achieved through a range of approaches including non-targeted (random) NGS of virus isolates amplified in cell culture or directly from patient samples. However, when input material is limited, low viral genome copy numbers necessitate a template-targeted approached followed by molecular amplification by PCR or iso-thermal amplification to generate sufficient nucleic acid for sequencing. Generally, these require knowledge of the virus genome and the design pairs of primers that anneal to the target genome. Perhaps the most popular method for SARS-CoV-2 sequencing is the 'ARTIC' approach (20), which can reliably identify SNVs and minority variants present in as little as 3% of genomes (21). However, the requirement for pairs of primers constrains where amplicons can be designed and imparts sensitivity to single nucleotide variants (SNVs). Multiple PCR reactions containing different pools of paired-primers must also be performed in order to obtain cDNA amplicons of the correct size and to prevent the interaction or mispriming of PCR primers. Importantly, pairs of primers that do not flank RNA recombination junctions will be unable to detect unexpected or unpredicted RNA recombinant species. Finally, paired-primer approaches also necessitate the redesign and validation of alternative sets of primer-pairs for each specific NGS platform used (e.g. Illumina amplicons are 200-500 nts. Nanopore amplicons are ~2000-5000nts).

To address these limitations and optimize the ability of NGS to quantify, all types of viral genetic variants, the inventors have combined 'ClickSeq' with tiled-amplicon approaches. ClickSeq (22, 23) is a click-chemistry based platform for NGS that prevents artifactual sequence chimeras in the output data (24). Using ClickSeq, the 3*end of an amplified cDNA segment is generated by the stochastic incorporation of terminating 3' azido-nucleotides (AzNTPs) during reverse transcription. A downstream adaptor is 'click-ligated' onto the cDNA using copper-catalyzed azide-alkyne cycloaddition (CuAAC). Therefore, 'Tiled-ClickSeq' only requires one template-specific primer per cDNA amplicon. To achieve whole genome sequencing of a virus isolate or sample, multiple tiled primers are designed evenly along the virus genome. Only one pool of RT-primers is required, even when >300 template specific primers and their corresponding cDNA amplicons are generated in the same reaction. This simplifies the assay design, and importantly removes constraints imposed in paired-primer strategies (25). Furthermore, the same primer set can be used for both Illumina and Nanopore platforms even when requiring different cDNA amplicon sizes. The library construction allows for additional quality control features including the use of unique molecular identifiers (UMIs) in the 'click-adaptor' as well as the ability to identify each RT-primer that gives rise to specific cDNA amplicon when using paired-read NGS. Here, the inventors utilize the Tiled-ClickSeq method to analyze multiple isolates of SARS-CoV-2 and demonstrate that 'Tied-ClickSeq' accurately reconstructs full-length viral genomes. The method also captures recombinant RNA species including sgmRNAs, SVs and D-RNAs. Overall, Tiled-ClickSeq therefore provides a convenient and robust platform for full genetic characterization of viral isolates.

Viruses and RNA extraction. For WRCEVA isolates, viral RNA was obtained from supernatant materials of viral isolates amplified on Vero cells originally obtained from nasopharyngeal swab samples that tested positive in clinical laboratory assays for SARS-CoV-2 RNA, as described previously (26). The use of deidentified human samples was approved by the UTMB IRB under protocol 20-0088. The recombinant wild-type and 'PRRA-deletion' mutant SARS-CoV-2 are based on the sequence of USA-WA1/2020 isolate provided by the WRCEVA as previously described (27, 28). Wild-type and mutant SARS-CoV-2 were titrated and propagated on Vero E6 cells. RNAs were extracted from either total cellular materials or supernatants as indicated in the main text.

SARS-CoV-2 reverse transcription primer design. A 'first' tiled-primer set (v1) containing 71 primers was designed cognate to the WA-1 SARS-CoV-2 genome (accession number: NC_045512.2) using the primalseq webserver (21) (primal.zibraproject.org/) with an amplicon distance of approximately 500nt in between each primer pair. The inventors used only the 'right' primer sequences generated by primalseq and appended the Illumina p7 adaptor to these (e.g., GTGACTGGAGTTCAGACGTGTGCTCTTCCGATCT (SEQ ID NO:1)+NNNN+TGTCTCACCACTACGACCGTAC (SEQ ID NO:2). The inventors also included an additional primer designed to target the 3'-most 25 nts of the SARS-CoV-2 genome. A 'second' tiled-primer set was synthesized in a similar fashion using 326 loci described previously (29). A 'third' tiled-primer pool (v3) was generated by combining the v1 and v2 pools. Primers used in this study are provided as BED files with their loci and corresponding sequence, see GenBank (MW047307-MW047318 and MW703487-MW703490), relevant sequences incorporated herein by reference. Each primer was pooled in equimolar ratios to yield a SARS-CoV-2 specific primer pool used for the RT step of Tiled-ClickSeq.

ClickSeq Library preps. Random-primer ClickSeq NGS libraries were synthesized as described in previously published protocols from our lab (23, 30). For Tiled-ClickSeq, the inventors made two important improvements: 1) firstly, the primers used to initiate reverse transcription comprise pools of 10s-100s of virus-specific primer oligos; and 2) the inventors anneal the RT-primers to the RNA template by incubating the RNA+primer mixture at 65° C. for 5 mins, followed by a slow-cool of 1 degree per minute to a final temperature or 12° C. RT-enzyme mixes are added at 12° C. and primer extension is performed for 10 mins at 55° C. All subsequent steps of the Tiled-ClickSeq reaction, comprising RT cleanup, click-ligation. PCR amplification and cDNA library size-selection are identical to those used in the random-primed ClickSeq method and described previously (23, 30). The i5 'Click-Adaptor' was a reverse complement of the full Illumina Universal Adaptor sequence, plus an additional twelve 'N's at 5'-end to provide a Unique Molecular Identifier and functionalized with a 5'-hexynyl group (IDT). Final NGS libraries containing fragment sizes ranging 300-700 nts were pooled and sequenced on Illumina MiSeq, MiniSeq or NextSeq platforms using paired-end sequencings.

Nanopore Sequencing. Final cDNA libraries generated by the Tiled-ClickSeq protocol, although containing Illumina adaptors, are compatible with the Direct Sequencing by Ligation Kit (LSK-109) provided by Oxford Nanopore Technologies. cDNA library fragments >600nts in length are gel extracted and processed for nanopore sequencing using the manufacturer's protocols. The addition of demultiplexing barcodes can be achieved using the Native Barcoding by Ligation module (NBD104), again following the manufacturer's protocols. Single-plex or pooled cDNA libraries with ONT adaptors were loaded onto MIN-FLO109 flowcells on a MinION Mk1C and sequenced using the MinKNOW controller software for >24 hours. Raw FAST5 reads were base-called and demultiplexed using Guppy.

Bioinformatics. For Illumina reads, raw data were filtered and trimmed using fastp (31) to remove Illumina adaptors, quality filter reads and extract Unique Molecular Identifiers (UMIs). A custom python3 script was written to split the raw 'forward'/R1 reads into multiple individual FASTQ files depending upon the tiled-sequencing primer that is present in the first 30 nts of the 'reverse'/R2 paired-read. These split FASTQ files were then trimmed using cutadapt (32) to remove primer-derived sequences from the R1 reads. After trimming, all the split R1 files were re-combined to yield a final processed dataset. These reads were mapped to the WA-1 strain (NC_045512.2) of SARS-CoV-2 using bowtie2 (33) and a new reference consensus genome was rebuilt for each dataset using pilon (34). Next, the inventors mapped the processed read data to the reconstructed reference genome using ViReMa (35) to map to both the virus and the host (ch1Sab2) genome. SAM files were manipulated using samtools (36) and de-duplicated using umi-tools (37). Minority variants were extracted using the mpileup command and a custom python3 script to count nucleotide frequency at each coordinate to find minority variants. Mapped data were visualized using the Tablet Sequence Viewer (38).

For Nanopore reads, porechop (github.com/rrwick:Porechop) was used to remove Illumina adaptor sequences and reads greater than 100nts in length were retained. These were mapped to the WA-1 SARS-CoV-2 genome (NC_045512.2) using minimap2 (39) with the—splice option selected. Output SAM files were processed using samtools (36) and bedtools (40) to generate coverage maps.

Data Availability Statement. All raw sequencing data (Illumina and Nanopore in FASTQ format) are available in the NCBI Small Read Archive with BioProject PRJNA707211. Consensus genomes for WRCEVA SARS-CoV-2 isolates reported in this manuscript are deposited at GenBank (MW047307-MW047318 and MW703487-MW703490).

Figure 4A:
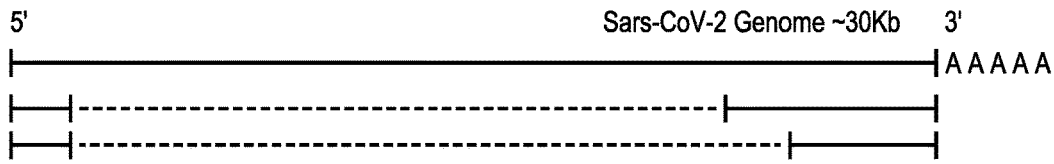
FIGS. 4A to 4F show a schematic of Tiled-ClickSeq and Computational Pipeline.
Figure 4B:
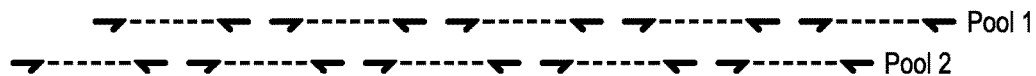
Figure 4C:
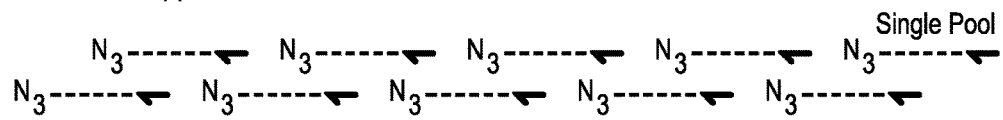
Figure 4D:
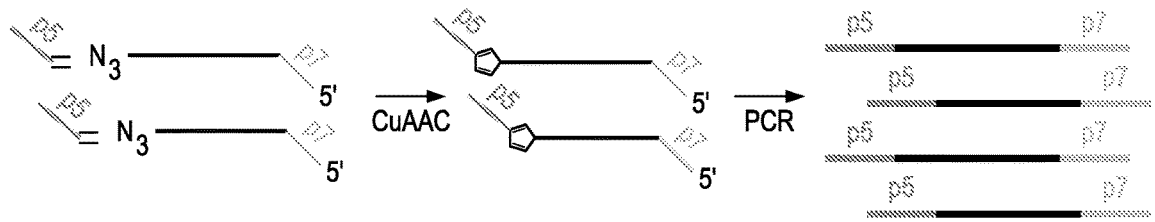
Figure 4E:
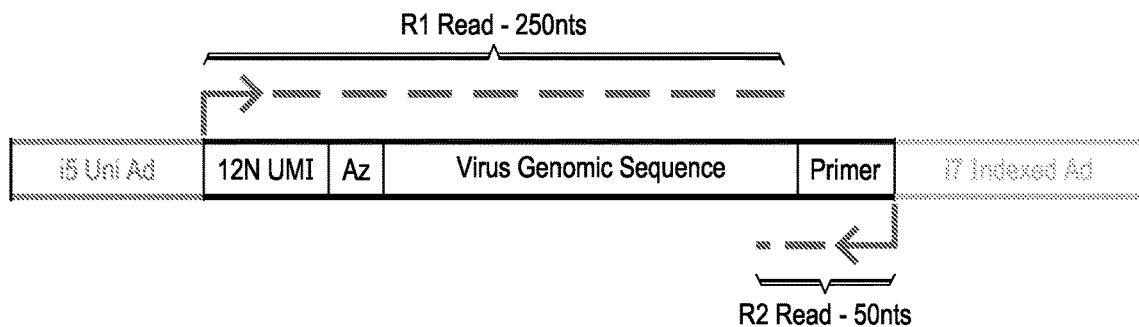
Figure 4F:
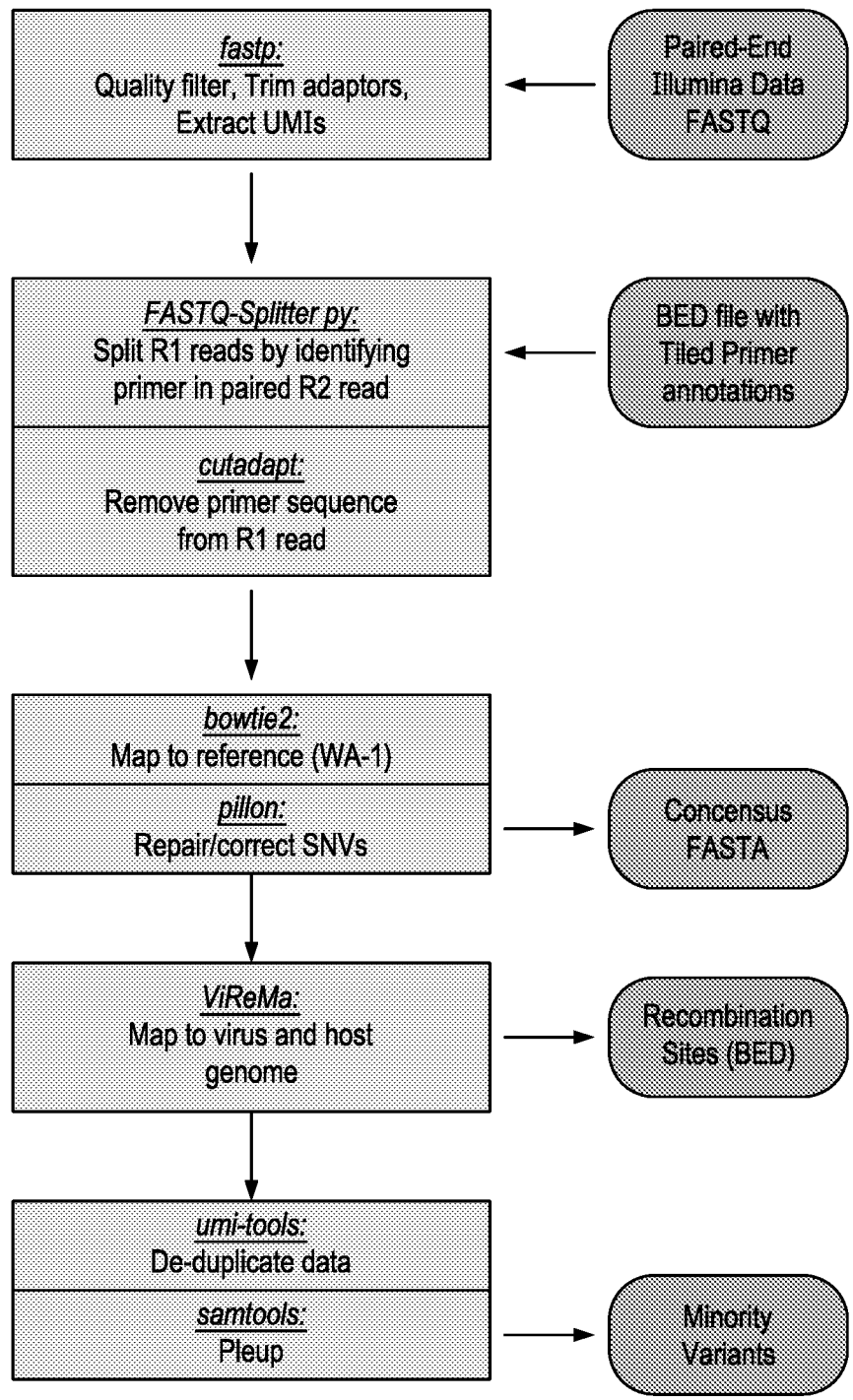

Overview of sequencing strategy. Most tiled approaches for complete viral genomes sequencing from viral isolates require the design of pairs of primers that generate predefined overlapping amplicons in multiple pools (FIGS. 4A, 4B). However, this can prevent the detection of recombinant viral genomic materials such as sub-genomic mRNAs (sgmRNAs) or Defective-RNAs (D-RNAs). To overcome these issues, the inventors designed a template directed tiled-primer approach to reverse transcribe segments of the SARS-CoV-2 genome based upon the 'ClickSeq' method for NGS library synthesis (30). Instead of random-hexamer or oligo-dT primers as used in ClickSeq and Poly(A)-ClickSeq, respectively (41), the inventors use multiple 'tiled' RT-primers designed at regular interval along the viral genome (FIG. 4C). In 'Tiled-ClickSeq', pooled primers initiate a reverse transcription in a reaction that has been supplemented with 3'-azido-nucleotides (AzNTPs). This yields stochastically terminated 3'-azido-cDNA fragments, which can be click-ligated onto a hexynyl-functionalized Illumina i5 sequencing adaptor (FIG. 4D). After click-ligation, the single-stranded triazole-linked cDNA is PCR-amplified using indexing p7 adaptors to fill in the ends of the NGS library, yielding the final library schema shown in FIG. 4E. The inventors designed the click-adaptor with an additional 12 random nucleotides at its 5' end. As each adaptor can only be ligated once onto each unique cDNA molecule, this provides a unique molecular identifier (UMI) (42). Due to the stochastic termination of cDNA synthesis in the RT step, a random distribution of cDNA fragments is generated from each primer, giving rise to the hypothetical read coverage. The lengths of these fragments, and thus the obtained read coverage can be optimized to ensure overlapping read data from each amplicon by adjusting the ratio of AzNTPs to dNTPs in the RT reaction (30). With this approach, the inventors found that the inventors could robustly make NGS libraries from as little as 8 ng of total cellular RNA with only 18 PCR cycles. Final libraries are excised from agarose gels (300-600nt cDNA size), pooled, and are compatible with Illumina sequencing platforms. A computational pipeline was compiled into a batch script depicted by the flow-chart in FIG. 4F.

Validation with WA-1 Strain. To test this approach, the inventors obtained 200 ng RNA from a SARS-CoV-2 isolate deposited at the World Reference Center for Emerging Viruses and Arboviruses (WRECEVA) at UTMB (26) and performed Tiled-ClickSeq using a 1:35 AzNTP:dNTP mix. NGS libraries were sequenced on an Illumina MiSeq (2×150 reads). Reads were quality processed using fastp (31) and mapped to the virus genome using bowtie2 (33). A 'sawtooth' pattern of read coverage over the genome was generated (FIG. 5) with 'teeth' appearing as expected upstream of each tiled primer. Peaks of coverage for each 'tooth' ranged from ~13000× to −100×. Overall, the inventors obtained genome coverage >25× from nucleotide 3 to 29823 (50nts from the 3' end of the genome). This depth is sufficient to reconstruct a consensus genome sequence which was found to be identical to that already deposited (MT020881) for this isolate (43).

Figure 5:
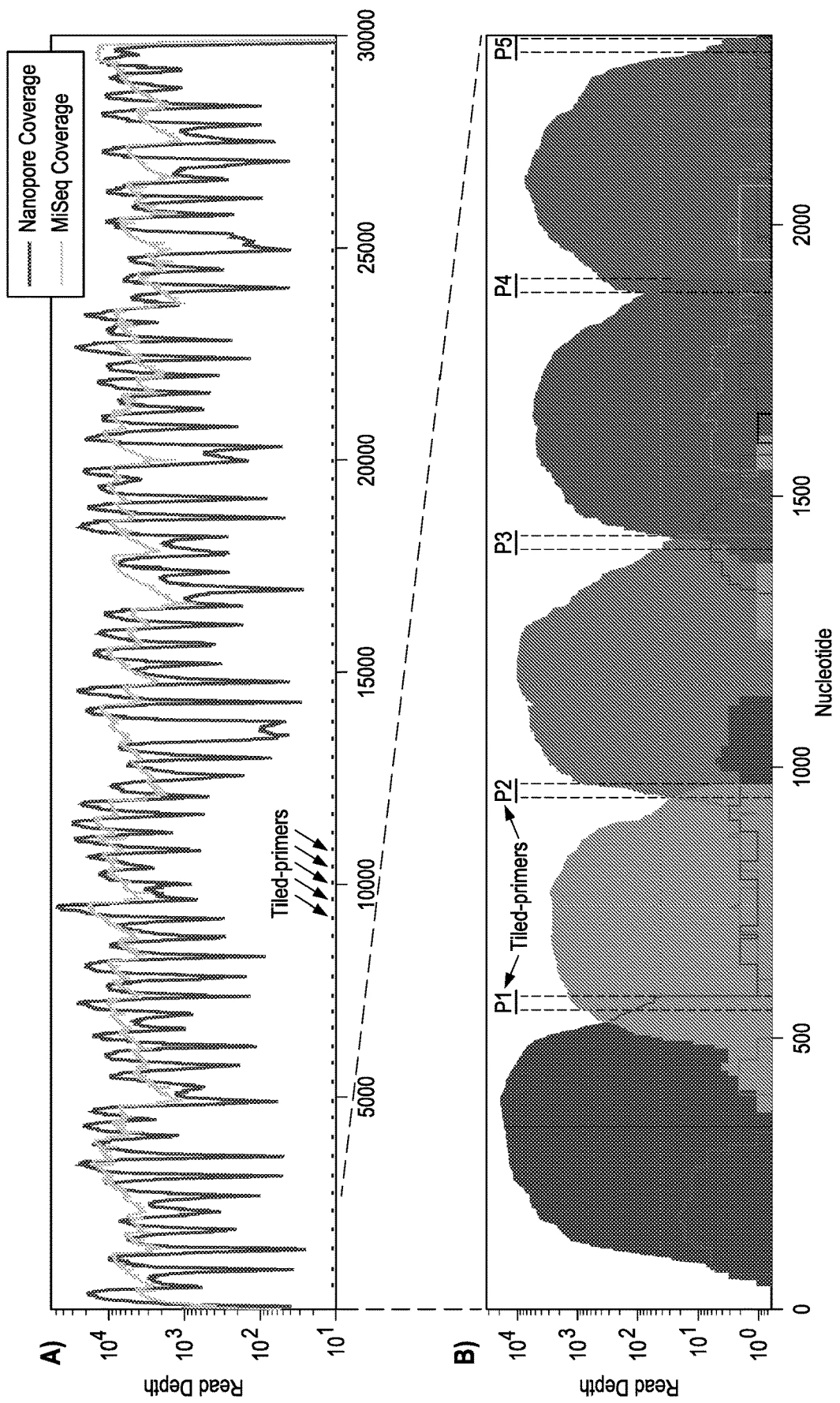
FIG. 5 shows the read coverage over the SARS-CoV-2 genome using Tiled-ClickSeq: (Top) Read coverage obtained from Tiled-ClickSeq over the whole viral genome is depicted when sequencing using an Illumina MiSeq or on an Oxford Nanopore Technologies MinION device. A 'saw-tooth' pattern of coverage is observed with 'teeth' upstream of tiled primers, indicated at the bottom of the plot by short black lines. Bottom: zoomed in read coverage of nts 1-2400 of the SARS-CoV-2 genome with read coverage from five individual primers colored to illustrate coverage from downstream amplicons overlapping the primer-binding sites of upstream tiled-primers.

When using paired-end sequencing, the 'forward'/'R1' read is derived from the click-adaptor and contains the UMI. The 'reverse'/'R2' read is derived directly from the tiled primer (see schematic in FIG. 4E). The inventors wrote a custom python3 script to split all the forward 'R1' reads into multiple individual FASTQ files based upon which primer generated each fragment. The mapping coverage obtained from five individual tiled-primers is shown in FIG. 5. The coverage for each primer (denoted by individual labels in FIG. 5) spans approximately 500-600 nts and extends 5'-wards from the tiled RT-primer. Read coverage from each primer overlaps the read coverage of the upstream primer. This allows for continuous gap-free read coverage over the viral genome which, importantly, allows a downstream cDNA amplicon to provide sequence information over and beyond an upstream primer. Additionally, the inventors were able to determine the frequency with which each primer either successfully maps to the viral genome, mis-primes from the host RNA, or gives rise to adaptor-dimers or other sequencing artifacts. This information can be used to identify primers that yield poor viral priming efficiency and therefore a more specific primer can be designed and substituted as needed.

For nanopore sequencing, the inventors also synthesized Tiled-ClickSeq libraries but using a 1:100 AzNTP:dNTP ratio to generate cDNA amplicons of increased lengths. The inventors retained cDNA fragments >600nts, yielding a few nanograms of dsDNA. This library, though containing the Illumina adaptors, can nonetheless be used as input in the default Oxford Nanopore Technologies (ONT) Ligation-Sequencing protocol (LSK-109) that appends ONT adaptors directly onto the ends of A-tailed dsDNA fragments. The inventors sequenced this library using an ONT MinION device and obtained 279,192 reads greater than 1 kbp in length. These were mapped to the WA-1 viral genome using minimap2 yielding continuous genome coverage (FIG. 5). A similar profile of read coverage to the Illumina data was observed, with peaks of coverage upstream of tiled-primer sites. The deeper dips in coverage were avoided however, due to the longer reads lengths that give greater overlap between cDNA amplicons.

Genome reconstruction of 12 Isolates: ClickSeq, Tiled-ClickSeq and Nanopore-Tiled-ClickSeq. To validate the suitability of Tiled-ClickSeq for whole virus genome reconstruction, the inventors obtained RNA extracted from 12 outgrowth samples of SARS-CoV-2 deposited at WRCEVA from nasopharyngeal swabs collected between March and April 2020. The inventors synthesized 12 Tiled-ClickSeq libraries and 12 random-primer ClickSeq libraries in parallel. These were submitted for sequencing on a NextSeq (2×150) yielding ~2-SM reads per sample (Table 3). Random-primed ClickSeq data were quality-filtered and adaptor trimmed using fastp (31) retaining only the forward R1 reads. Tiled-ClickSeq read data were processed and mapped following the scheme in FIG. 4F.

TABLE 3

Read counts and mapping rates for random-primed versus Tiled-ClickSeq approaches

| Sample | Outgrowth CT | ClickSeq Reads | Virus Mapped | % Viral Reads | Tiled v1 Reads | Virus Mapped | % Viral Reads |
|---|---|---|---|---|---|---|---|
| WRCEVA_00501 | 12.9 | 4,665,869 | 116,036 | 2.5% | 2,359,795 | 2,204,750 | 93.4% |
| WRCEVA_00502 | 12.9 | 4,989,513 | 118,260 | 2.4% | 1,962,581 | 1,820,925 | 92.8% |
| WRCEVA_00505 | 12.7 | 3,894,325 | 71,809 | 1.8% | 2,779,672 | 2,482,854 | 89.3% |
| WRCEVA_00506 | 12.5 | 4,979,989 | 108,532 | 2.2% | 2,395,750 | 2,148,256 | 89.7% |
| WRCEVA_00507 | 12.9 | 5,659,073 | 161,059 | 2.8% | 2,056,670 | 1,867,012 | 90.8% |
| WRCEVA_00508 | 16.8 | 3,987,009 | 91,452 | 2.3% | 1,787,418 | 1,433,005 | 80.2% |
| WRCEVA_00509 | 17.1 | 4,057,928 | 57,424 | 1.4% | 2,202,661 | 1,856,633 | 84.3% |
| WRCEVA_00510 | 16.2 | 5,328,829 | 65,281 | 1.2% | 2,040,332 | 1,601,544 | 78.5% |
| WRCEVA_00513 | 16.0 | 4,391,175 | 69,169 | 1.6% | 1,641,213 | 1,455,991 | 88.7% |
| WRCEVA_00514 | 12.9 | 4,340,084 | 84,211 | 1.9% | 2,089,241 | 1,902,748 | 91.1% |
| WRCEVA_00515 | 15.7 | 5,416853 | 102,179 | 1.9% | 2,205,166 | 1,915,129 | 86.8% |
| WRCEVA_00516 | 17.4 | 4,290,929 | 61,017 | 1.4% | 1,988,939 | 1,715,448 | 86.2% |

Figure 6A:
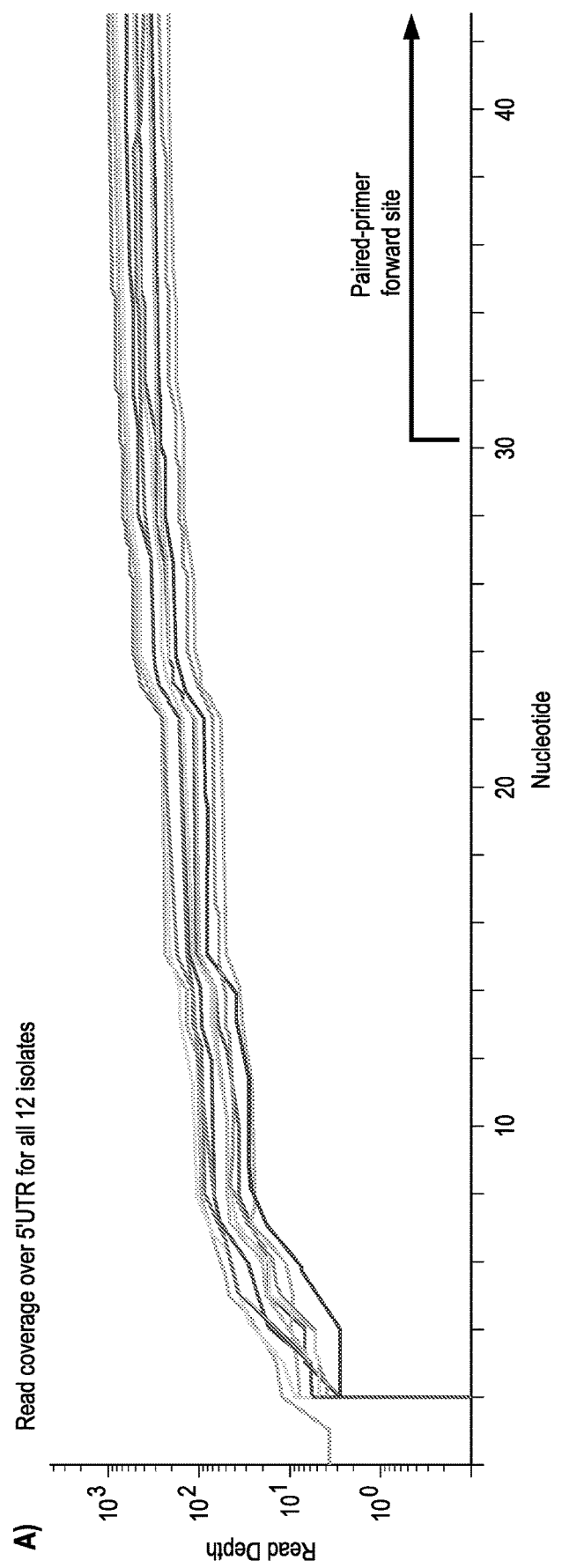
FIGS. 6A to 6C show a Genome Reconstruction of 12 SARS-CoV-2 isolates deposited at the World Reference Center for Emerging Viruses and Arboviruses (WRCEVA)
Figure 6B:
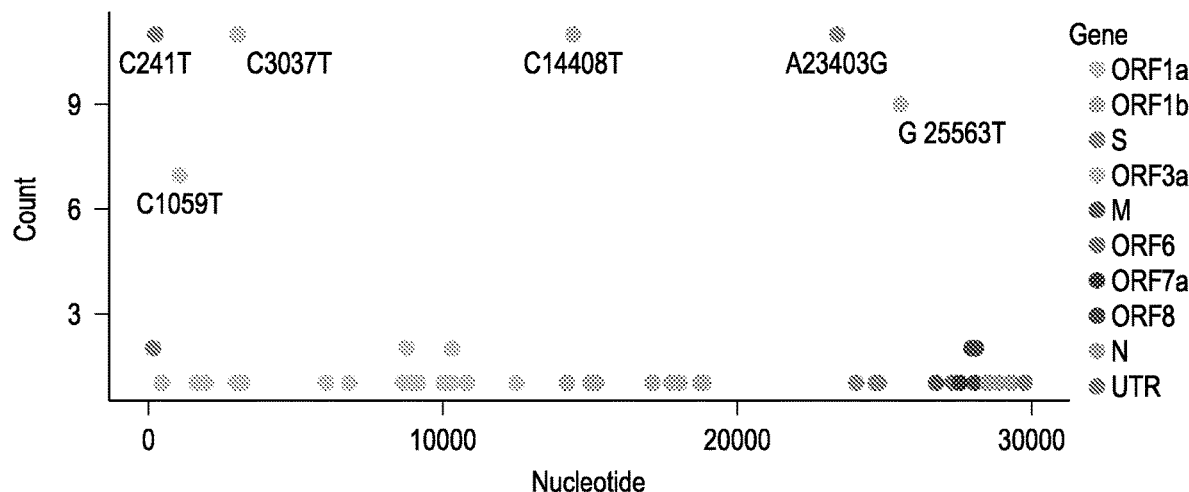

In the Tiled-ClickSeq data, after UMI deduplication, each isolate had an average coverage between 4,500-7,500 reads and a coverage of 25 reads in greater than 99.5% (29753/29903 nts) of the SARS-CoV-2 genome. Read coverage was also obtained covering the 5'UTR of each strain (>25 reads for all isolates from nucleotide 3 onwards (FIG. 6A). When using paired-primer approaches, the 5'UTR is ordinarily obscured by the 5'-most primer used in each pool (nts 30-54 for the ARTIC primer set depicted in FIG. 6A). As the 5' end is resolved here due to stochastic incorporation of a single AzNTP in a template-specific manner, the entirety of the viral genome can be resolved. The inventors reconstructed reference genomes from mapped reads using pilon (34) requiring 25× coverage for variant calling. In all cases, the reconstructed reference genomes were identical with or without controlling for PCR duplicates using the UMIs. The inventors found 5-12 SNVs per viral genome, including the prevalent D614G (A23403G) spike adaptation, which enhances SARS-CoV-2 transmission (44), in 11 out of the 12 isolates (FIG. 6B).

Figure 6C:
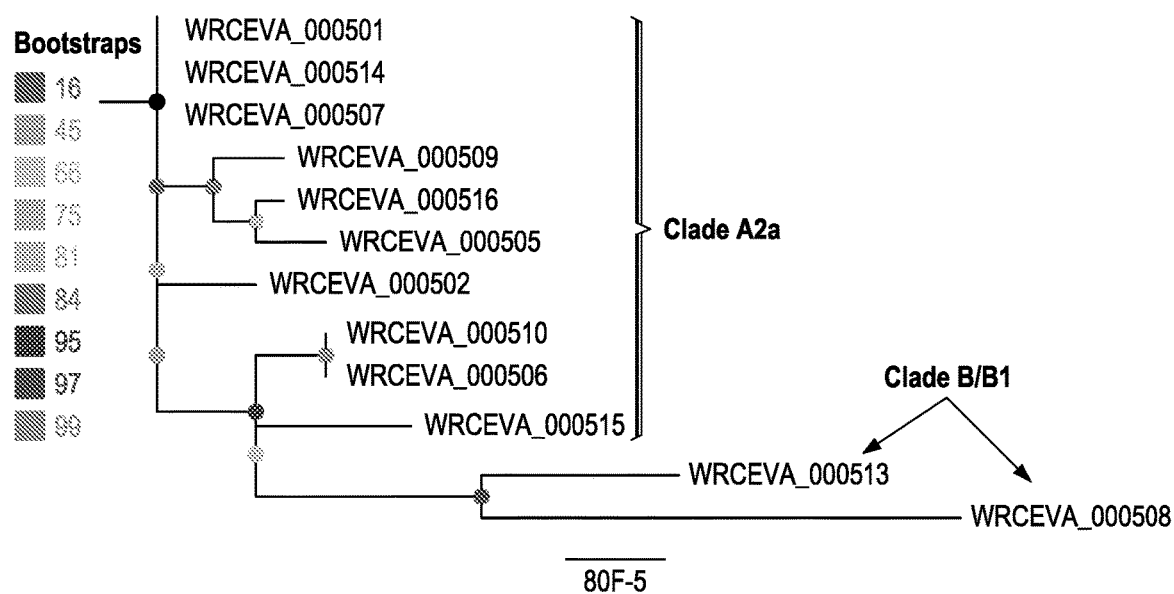

Genome reconstructions was similarly performed using the random-primed ClickSeq data reads. Identical genomes to the Tiled data were obtained for 11 out of 12 isolates, with only one SNV difference in one sample (WRCEVA_000510: T168C). In this case, the read coverage was too low in the random-primed data for pilon to report an SNV. Nevertheless, visual inspection of the mapped data revealed that all nucleotides at this locus were indeed C's, as reported for the Tiled-ClickSeq data. Phylogenetic tree reconstruction using NextStrain (45) placed 10 of the isolates in the A2a clade (FIG. 6C). Three of these isolates (WRCEVA_00506, WRCEVA_00510, WRCEVA_00515) were most closely related to European ancestors. Two isolates (WRCEVA_00508, WRCEVA_00513) were Clade B/B1 most closely related to Asian ancestors. Together, these data thus supported a model for multiple independent introductions of SARS-CoV-2 into the USA and subsequently into Galveston, Texas.

The inventors also retained cDNA fragments >600 bps from the Tiled-ClickSeq libraries and sequenced these using an ONT MinION device. The inventors used the ONT native barcoding kit to multiplex the 12 samples and the Ligation-Sequencing protocol (LSK-109) to generate final libraries. Reads were mapped with minimap2 (39) yielding at least 100× coverage over >99.6% of the genome for each isolate. Again, reference genomes were reconstructed from the mapped data using pilon. With the exception of WRCEVA_000514 which contained a single additional SNV (C14220T), the reference genomes reconstructed from the nanopore data were identical to those generated from the Tiled-ClickSeq Illumina data. These data illustrate that Tiled-ClickSeq performs as well as random-primed methods either on Illumina or Nanopore platforms for whole genome reconstruction.

Minority Variants. The initial primer design (v1) (FIG. 7A) successfully yielded coverage suitable for complete genome reconstruction. However, some regions still received low coverage with fewer than a 100 deduplicated reads, preventing identification of minority variants in these regions. Therefore, the inventors redesigned our primer scheme by adding an additional 326 primers (v2) previously reported (29) for tiled coronavirus sequencing to make a pool comprising a total of 396 unique primers (v3). The inventors re-sequenced the 12 WRCEVA isolates analyzed as described above plus an additional four that subsequently became available. An example of mapping coverage for isolate WCREVA_000508 is illustrated in FIG. 7A, where the coverage over the viral genome is more even with less extreme ranges of read depth.

Using the R2 read, the inventors can determine which primer gives rise to each R1 read and trim primer-derived nucleotides from the R1 read. This is an important quality control as it prevents the assignment (or failure thereof) of SNVs and/or the mapping of recombination events due to primer mis-priming. If reads are mapped without trimming away the primer-derived nucleotides found in the R1 read (as depicted in FIG. 7B), the inventors see numerous high frequency (2-50%) minority variants. The majority of these apparent minority variants overlap primer-target sites and are likely artefactual. Furthermore, the same high-frequency events are often seen across multiple independent samples. To control for this, the inventors map reads after trimming away primer-derived nucleotides from the R1 reads as per our pipeline described above (schematic in FIG. 1F). Finally, to control for PCR duplication events, the inventors make use of the UMIs embedded in the click-adaptor. The final de-duplicated mapped, primer-trimmed reads (FIG. 7C) provide a robust readout of minority variants in these isolates (Table 4). Across 10 WRCEVA isolates the inventors found only 26 minority variants present at >2% all of which were unique within this dataset. Six isolates reported no minority variants at all.

TABLE 4

Minority variants and rates (>2%) found across 16 WRCEVA isolates

| Sample | Nt | Nuc | Read Depth | A | U | G | C | Variant Rate | Location | Result |
|---|---|---|---|---|---|---|---|---|---|---|
| WRCEVA_000501 | 12049 | C | 2116 | 0 | 95 | 1 | 2020 | 4.5% | ORF1ab | N3928K |
| WRCEVA_000502 | 10207 | C | 2240 | 0 | 118 | 0 | 2122 | 5.3% | — | — |
| WRCEVA_000502 | 16050 | U | 3853 | 0 | 3322 | 0 | 531 | 13.8% | — | — |
| WRCEVA_000502 | 17489 | A | 4597 | 4433 | 162 | 1 | 1 | 3.6% | ORF1ab | E5742V |
| WRCEVA_000502 | 21526 | A | 8749 | 6508 | 0 | 2240 | 1 | 25.6% | ORF1ab | I7088V |
| WRCEVA_000503 | 14220 | C | 1638 | 1 | 463 | 0 | 1174 | 28.3% | — | — |
| WRCEVA_000504 | 1556 | A | 2828 | 2499 | 0 | 328 | 2723 | 11.6% | ORF1ab | I431V |
| WRCEVA_000504 | 27925 | C | 2857 | 0 | 134 | 0 | 1 | 4.7% | ORF8 | T11I |
| WRCEVA_000507 | 19515 | A | 2393 | 2295 | 1 | 97 | 0 | 4.1% | — | — |
| WRCEVA_000508 | 9756 | G | 1376 | 28 | 0 | 1348 | 0 | 2.1% | ORF1ab | R3164H |
| WRCEVA_000508 | 26056 | G | 2092 | 0 | 86 | 2006 | 0 | 4.1% | ORF3a | D222Y |
| WRCEVA_000508 | 27556 | G | 2066 | 128 | 0 | 1938 | 0 | 6.2% | ORF7a | A55T |
| WRCEVA_000509 | 11956 | C | 1962 | 0 | 199 | 0 | 1763 | 10.1% | — | — |
| WRCEVA_000509 | 17245 | C | 4062 | 2 | 470 | 0 | 3590 | 11.6% | ORF1ab | R5661C |
| WRCEVA_000509 | 18005 | U | 5408 | 1 | 4949 | 458 | 0 | 8.5% | ORF1ab | L5915R |
| WRCEVA_000509 | 25569 | U | 3448 | 4 | 3326 | 113 | 5 | 3.5% | — | — |
| WRCEVA_000509 | 27919 | U | 839 | 0 | 809 | 0 | 30 | 3.6% | ORF8 | 19T |
| WRCEVA_000509 | 28767 | C | 2011 | 0 | 109 | 0 | 1902 | 5.4% | N | T165I |
| WRCEVA_000511 | 3003 | U | 2880 | 79 | 2787 | 1 | 13 | 2.7% | ORF1ab | V913E |
| WRCEVA_000511 | 10738 | U | 4580 | 0 | 4440 | 0 | 140 | 3.1% | — | — |
| WRCEVA_000511 | 25892 | U | 133 | 0 | 130 | 0 | 3 | 2.3% | ORF3a | I167T |
| WRCEVA_000511 | 28001 | G | 1414 | 1 | 29 | 1384 | 0 | 2.1% | — | — |
| WRCEVA_000513 | 27046 | C | 5539 | 0 | 138 | 0 | 5401 | 2.5% | M | T175M |
| WRCEVA_000514 | 11603 | A | 5405 | 5075 | 0 | 330 | 0 | 6.1% | ORF1ab | M3780V |
| WRCEVA_000514 | 26526 | G | 525 | 0 | 20 | 505 | 0 | 3.8% | M | A2S |

RNA Recombination: sgmRNAs, Structural variants and Defective RNAs. To characterize RNA recombination, the inventors used our bespoke ViReMa pipeline (35) to map RNA recombination events in NGS reads that correspond to either sgmRNAs, SVs or D-RNAs. ViReMa can detect agnostically a range of expected and unusual RNA recombination events including deletions, insertions, duplications, inversions as well as virus-to-host chimeric events and provides BED files containing the junction sites and frequencies of RNA recombination events. The inventors mapped the Tiled-ClickSeq data to the corrected reference genome for each WRCEVA isolate using ViReMa. The inventors also took total cellular RNA and RNA extracted from the supernatants of Vero cells transfected with RNA derived from an in vitro infectious clone of SARS-CoV-2 (icSARS-CoV-2) (27). These clone-derived RNAs contained either the WT SARS-CoV-2, or were engineered with a deletion near the furin cleavage site of the spike protein, which the inventors recently demonstrated is a common adaption to Vero cells and which alters SARS-CoV-2 pathogenesis in mammalian models of infection (28).

The identities and frequencies of the 13 most abundant RNA recombination events are illustrated in FIG. 8A. The inventors found all the expected sgmRNAs previously annotated for SARS-CoV-2 (46) as well as non-canonical sgmRNAs. The inventors found that sgmRNAs were highly enriched in the cellular fractions from expressed icSARS-CoV-2 isolates (comprising >95% of the total viral genetic materials) but were relatively depleted in the supernatant fraction. This reflects a strong restriction of the packaging of these RNA species into virions. In the icSARS-CoV-2 samples. Tiled-ClickSeq and ViReMa accurately reported the expected deletion (Δ23603^23616). Interestingly, the inventors also identified small structural variants (Δ23583^23599) in seven of the WRCEVA isolates with a frequency of 2-50%, similar to reports of the selection of variants containing deletions at this site after in vitro passaging on Vero cells (47). The inventors also found a novel SV in one isolate (WRCEVA_000504: Δ27619^27642) present in 3.5% of the reads resulting in an 8 amino acid deletion in ORF7a. The inventors additionally identified a small number of micro-indels (Table 5) in some isolates.

and D-RNAs. The targeted approach requires a relatively small number of reads to be collected, allowing 10s of samples to be processed on a MiSeq platform or potentially 100s on a single flowcells of a NextSeq. Furthermore, the same library preps can be used as input in Oxford Nanopore Sequencing pipelines to yield longer reads, providing the convenience and portably inherent to the platform. The inventors demonstrated that this method can be used to reconstruct full length SARS-CoV-2 genomes in a manner equivalent to random-primed methods. Full length-genome sequencing is achieved, including the 5'UTR, missed in the bulk of current high-throughput sequencing efforts, removing the need for 5'RACE.

The design of Tiled-ClickSeq imparts built-in quality control tools, including UMIs in the click-adaptor and the opportunity to use paired-end sequencing to identify the primer that gives rise to each amplicon. For example, a unique molecular identifier can be added to the click-adaptor that provides certain benefits including: quality control (control for PCR duplication events) and/or the ability to identify the primer that gives rise to each amplicon. In addition to controlling for aberrant SNVs, minority and structural variants, this information can be used to determine the relative sensitivity and specificity of each primer in the primer mix allowing the scheme to be pruned and optimized.

TABLE 5

Micro-indels and rates (>2%) found across 16 WRCEVA isolates

| Sample | MicroInDel | Nucs | Variant Rate | Location | Result |
|---|---|---|---|---|---|
| WRCEVA_000502 | Δ519^523 | UGGUU | 2.2% | ORF1AB | Frameshift |
| WRCEVA_000504 | Δ29686^29693 | CAGUGUGU | 3.5% | 3'UTR | — |
| WRCEVA_000505 | Δ519^523 | UGGUU | 2.9% | ORF1AB | Frameshift |
| WRCEVA_000506 | Δ519^523 | UGGUU | 3.8% | ORF1AB | Frameshift |
| WRCEVA_000509 | Δ1237^1239 | UCA | 2.9% | ORF1AB | ΔH325 |
| WRCEVA_000510 | Δ686^694 | AAGUCAUUU | 5.1% | ORF1ab | ΔLSF141-143 |
| WRCEVA_000511 | Δ519^523 | UGGUU | 3.7% | ORF1AB | Frameshift |
| WRCEVA_000511 | Δ10811^10813 | CUU | 3.1% | ORF1AB | ΔL3516 |
| WRCEVA_000512 | Δ29750^29759 | GAUCGAGUG | 10.0% | 3'UTR | — |

Finally, the inventors observed thousands of RNA recombination events corresponding to D-RNAs. Despite their individual low frequencies, these events (displayed as a Recombination Heatmap in FIG. 8B) reveals interesting features of D-RNAs of SARS-CoV-2. Apparent duplication events or insertions were most commonly observed with recombination events enriched around the 3'UTR of the genome, consistent with our previous characterization of RNA recombination in distinct coronavirus isolates including MHV, MERS and SARS-CoV-2 (48). Finally, large deletions comprising RNA recombination events stretching from nucleotides ~6000-7000 to the 3'UTR were also observed, again, consistent with our previous observations. Altogether, these results demonstrate RNA recombination is a common and conserved feature of SARS-CoV-2 and that the emergence of D-RNAs is prevalent source of genetic diversity amongst these isolates and is captured using Tiled-ClickSeq.

Thus, the Tiled-ClickSeq provides a simple method for whole genome sequencing of virus isolates such as SARS-CoV-2 that can simultaneously map SNVs, minority variants as well as recombination events. Importantly, having only a single template-targeted primer per amplicon provides the opportunity to sequence any RNA template regardless of what expected or unknown sequence is found upstream, including recombinant RNA molecules such as sgmRNAs Our final primer scheme contained over 390 unique SARS-CoV-2 primers. This purposely thorough design demonstrates how the Tiled-ClickSeq pipeline can accommodate complex mixtures of overlapping primers within the same RT reaction. This built-in redundancy reduces the chance of primer dropout due to the presence of SNVs, SVs or recombination events found in primer-annealing sites. This feature is especially important considering the emergence of SARS-CoV-2 variants with deletions and mutations that disrupt sequencing efforts (49). Interestingly, the inventors detected very few minority variants in in our samples present above 2%. This is consistent with other reports of minority variant detection in SARS-CoV-2 isolates and likely reflects the well-characterized activity of the coronavirus ExoN-nsp14 as a 'proof-reader' enzyme (50). As a result, the greatest source of genetic diversity in coronavirus isolates may well be due to RNA recombination.

On the nanopore sequencing platform, the inventors obtained sequence reads within the same day as RNA extraction. While the baseline accuracy rate of the nanopore platform prevents the reliable annotation of minority variants present at <5%, this platform can reconstruct novel SARS-CoV-2 variants as well as identify abundant sgmRNAs longer reads. Nanopore sequencing also allows for identification of long-range epistatically linked variants. Epistatic linkage can also be computationally leveraged to identify minority variants present at levels below the baseline error-rate of the sequencing platform, for example, using CliqueSNV (51) or CoVaMa (52). Therefore, the nanopore platform in combination with Tiled-ClickSeq provides a robust pipeline for high-throughput SARS-CoV-2 variant detection with minimal infrastructure.

The ARTIC protocol contains a primer cognate to the 5'UTR of SARS-CoV-2 (nts 30-54) to capture and quantitate sub-genomic mRNAs (53). However, recombination events including non-canonical sgmRNAs will be missed by primer-pools that do not happen to flank RNA recombination junctions. In contrast, Tiled-ClickSeq is capable of 'agnostically' detecting any unanticipated RNA recombination including D-RNAs that can be characterized by RNA recombination events in or between any region of the viral genome, often in an unpredictable manner. As ClickSeq was originally designed to avoid artefactual recombination with fewer than 3 artefactual chimeric reads found per million reads, Tiled-ClickSeq provides a useful tool to identify D-RNAs and to robustly characterize rates of RNA recombination. Together, using the Tiled ClickSeq approach, the inventors are able to identify rare and unexpected recombination events and are not biased by the limitation of primer-pair approaches. Coupled with its cross-sequencing platform capabilities, the work highlights the utility of Tiled-ClickSeq for analysis using SARS-CoV-2 as an example.

Example 3. Individual Arbovirus Viral Genomes

Tiled-ClickSeq can identify individual viral genomes even when pools of different virus-specific tiled primers are used. Five sets of virus-specific Tiled-ClickSeq primers were designed (approach is described in Example 2) to five arboviruses: Chikungunya virus (CHIKV), Zika virus, Dengue virus 2. Yellow Fever virus (YFV) and West Nile virus. A single pool of each of these primers sets was used to generated Tiled-ClickSeq NGS libraries. Experimentally infected mosquitoes were diluted in uninfected mosquitoes in either a 1:20 or 1:40 ratio and RNA was extracted from this pool (provided by Weaver lab to the Routh Lab as part of the WAC-EID center). The identity of the virus present in each pool was not provided to the Routh Lab. Tiled-ClickSeq libraries targeting the five arboviruses were synthesis and sequence on a MiSeq, as described previously in Jaworski et al, 2021, bioRxiv. The Illumina reads where then mapped to the reference genomes for the five arboviruses. The table in the slide indicated the number of reads that mapped to each RNA virus for each sample. The cells shades in grey indicate which virus was present in the original experimentally infected mosquito (this information was later provided by the Weaver lab after analysis). As can be seen in the table, each sample has 100's to 1000's of sequence reads that map to the correct, expect virus genome. These data demonstrate that multiple RNA viruses can be targeted in a single Tiled-ClickSeq assay and correctly identify and sequence the viral genome in settings that closely recapitulate setting expected during surveillance settings.

TABLE 6

Results from using Tiled-ClickSeq libraries targeting the five arboviruses.

| Sample | Dilution | Chik | Zika | Dengue | YFV | West Nile |
|---|---|---|---|---|---|---|
| 9 | 1 in 20 | 12,226 | 1 | 1 | 0 | 0 |
| 10 | 1 in 20 | 14,506 | 0 | 0 | 0 | 0 |
| 11 | 1 in 20 | 0 | 7,775 | 0 | 1 | 0 |
| 12 | 1 in 20 | 0 | 47,367 | 0 | 0 | 0 |

TABLE 6-continued

Results from using Tiled-ClickSeq libraries targeting the five arboviruses.

| Sample | Dilution | Chik | Zika | Dengue | YFV | West Nile |
|---|---|---|---|---|---|---|
| 13 | 1 in 20 | 0 | 0 | 172 | 0 | 0 |
| 14 | 1 in 20 | 0 | 0 | 2,329 | 0 | 0 |
| 15 | 1 in 20 | 0 | 2 | 0 | 2,090 | 0 |
| 16 | 1 in 20 | 2 | 0 | 0 | 840 | 0 |
| 17 | 1 in 40 | 751 | 0 | 0 | 0 | 0 |
| 18 | 1 in 40 | 2,433 | 0 | 0 | 0 | 0 |
| 19 | 1 in 40 | 0 | 4094 | 0 | 0 | 0 |
| 20 | 1 in 40 | 0 | 14,886 | 0 | 0 | 0 |
| 21 | 1 in 40 | 0 | 0 | 4,666 | 0 | 0 |
| 22 | 1 in 40 | 0 | 0 | 3,629 | 0 | 0 |
| 23 | 1 in 40 | 1 | 0 | 0 | 23 | 0 |
| 24 | 1 in 40 | 0 | 0 | 0 | 522 | 4 |

Example 5. HIV Sequencing

Figure 9:
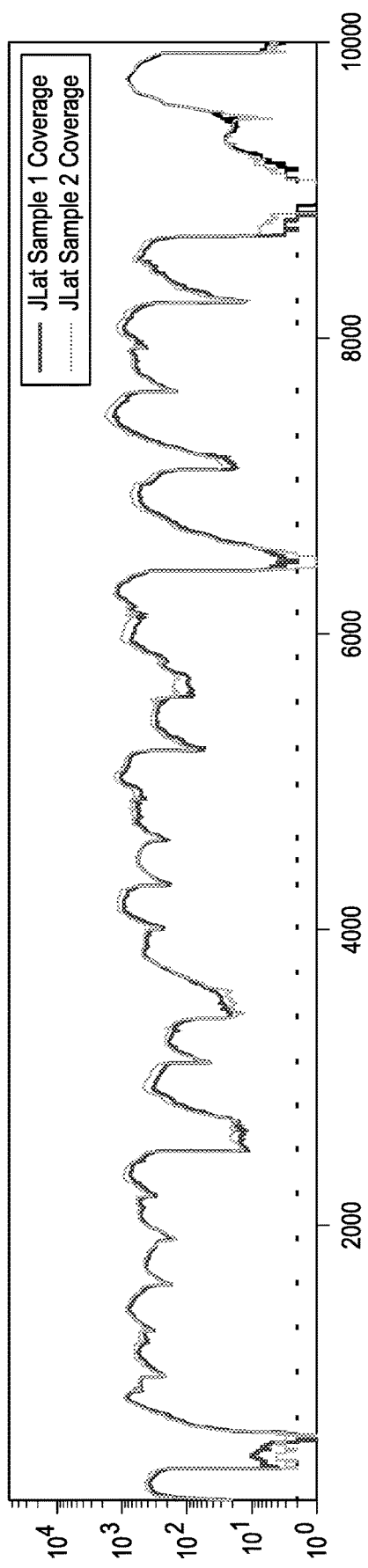
FIG. 9 shows total cellular RNA was extracted from two independent pools of induced J-Lat 10.4 cell-lines, that contain a single insert of a GFP/ENV-pseudo-typed HIV provirus. HIV-specific tiled-primers were designed along the HIV genome at sites indicated in the graph by the small horizontal blue lines at y=1. Tiled read coverage is shown across the viral genome (coordinates or HIV genome on x-axis, read coverage on y-axis) for the two independent experiments.
Figure 10:
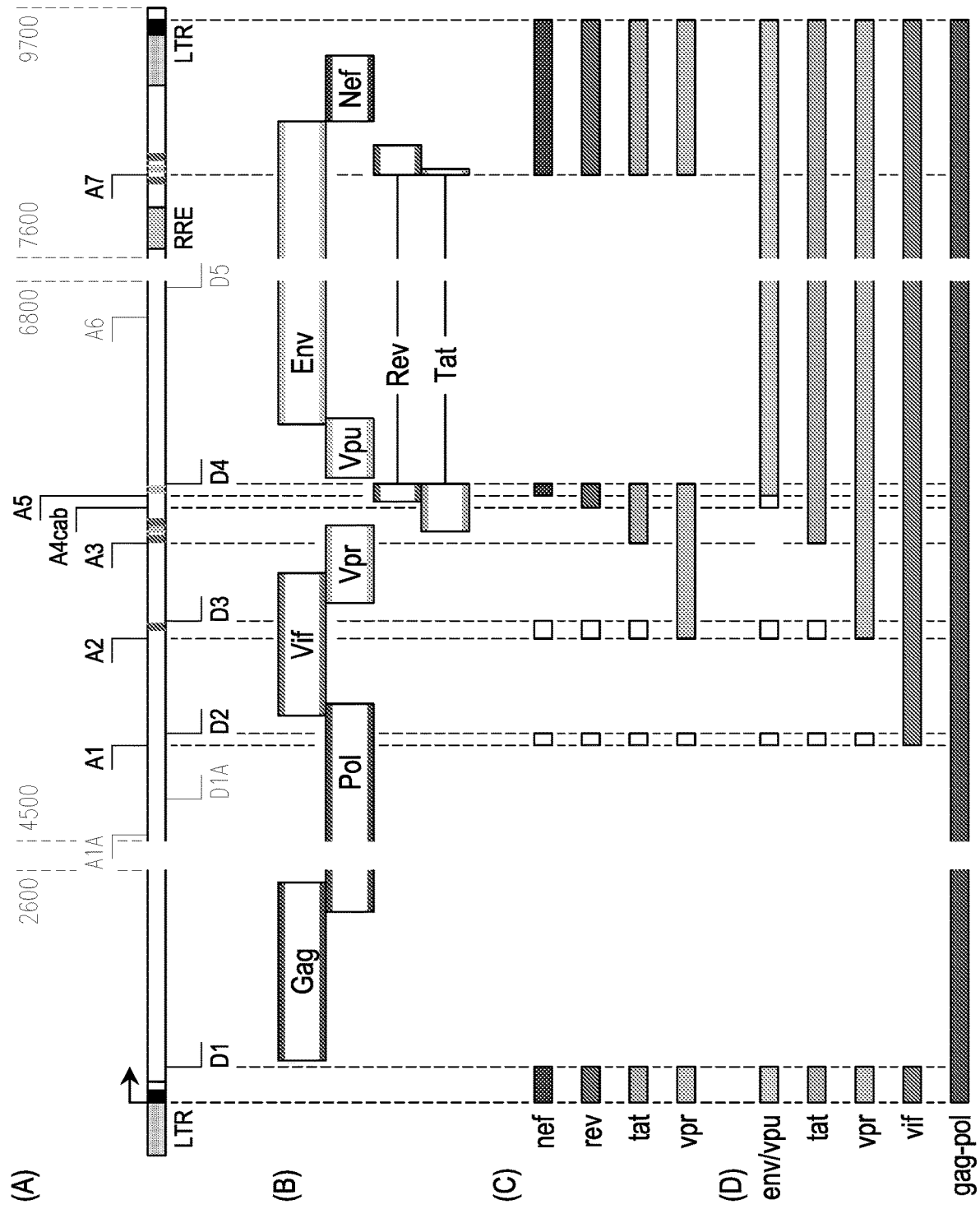
FIG. 10 shows Tiled-ClickSeq reads were also mapped to the viral genome to identify common HIV mRNA splice events. A schematic of HIV splicing is shown on the Left (adapted from Saliou et al, Frontiers in Bioscience, 2009), with canonical donor (D) and acceptor (A) sites indicated. Examples Tiled-ClickSeq reads that mapped over select splice events are depicted (visualized using Tablet Sequence Visualizer) over D1-A4a, D1-A4b, D1-A5 Splice sites (upper right) and genome and D2-A5 Splice site (lower right). Arrows indicate individual reads that map over splice junctions.

FIG. 9 shows total cellular RNA was extracted from two independent pools of induced J-Lat 10.4 cell-lines, that contain a single insert of a GFP/ENV-pseudo-typed HIV provirus. HIV-specific tiled-primers were designed along the HIV genome at sites indicated in the graph by the small horizontal blue lines at y=1. Tiled read coverage is shown across the viral genome (coordinates or HIV genome on x-axis, read coverage on y-axis) for the two independent experiments. FIG. 10 shows Tiled-ClickSeq reads were also mapped to the viral genome to identify common HIV mRNA splice events. A schematic of HIV splicing is shown on the Left (adapted from Saliou et al. Frontiers in Bioscience, 2009), with canonical donor (D) and acceptor (A) sites indicated. Examples Tiled-ClickSeq reads that mapped over select splice events are depicted (visualized using Tablet Sequence Visualizer) over D1-A4a. D1-A4b. D1-A5 Splice sites (upper right) and genome and D2-A5 Splice site (lower right). Arrows indicate individual reads that map over splice junctions.

In one embodiment, the present invention includes a method of single-primer tiled sequencing comprising, consisting essentially of, or consisting of: reverse transcribing a target nucleic acid with multiple tiled primers spaced along a genome, each only targeting one annealing site to form amplicons in the presence of terminating 3' azido nucleotides to incorporate the terminating 3' azido nucleotides into the cDNA; click-ligating a downstream primer onto the 3' azido terminated cDNA such that a template-specific primer is not required; amplifying the click-ligated cDNA; and sequencing the amplicons. In one aspect, the target nucleic acid is a partial or whole viral or bacterial genome or a sub-genomic viral genome. In another aspect, the target nucleic acid is a whole genome or a sub-genomic genome or an RNA or DNA transcript derived from the parental genome. In another aspect, the target nucleic acid is either deoxyribonucleic acid (DNA) or ribonucleic acid (RNA). In another aspect, the amplification reaction is a PCR or iso-thermal amplification reaction, or wherein the amplification step occurs without the need to design corresponding paired PCR or iso-thermal amplification reaction primers. In another aspect, the sequencing is by an automated process on a chip, Sanger sequencing. Maxam-Gilbert sequencing, dye terminator sequencing, sequencing by synthesis, pyro-sequencing, microarray hybridization, next-generation sequencing methods, next-next-generation sequencing, ion semiconductor sequencing, polony sequencing, sequencing by ligation. DNA nanoball sequencing, or single molecule sequencing. In another aspect, the amplicons are 100-10.000 nucleotides in length. In another aspect, the method only requires one template-specific primer per amplicon. In another aspect, the sequences of the multiple tiled primer sequences are selected along the virus genome. In another aspect, the sequences of the multiple tiled primer sequences are selected along two or more different viral genomes in parallel. In another aspect, the sequences of the multiple tiled primer sequences only target one annealing site. In another aspect, the target nucleic acid is sequenced without the need to design corresponding paired PCR primers. In another aspect, the wherein the downstream primer comprises a unique molecular identifier, which is a sequence such as a barcode that allows for identification of the individual downstream primer or click-adaptor.

In another embodiment, the present invention includes a method of single-primer tiled whole or partial viral genome or multiple genome, sequencing comprising, consisting essentially of, or consisting of: reverse transcribing a target viral nucleic acid with multiple tiled primers spaced along a genome, each only targeting one annealing site to form amplicons, in the presence of terminating 3' azido nucleotides to incorporate the terminating 3' azido nucleotides into the cDNA; click-ligating a downstream primer onto the 3' azido terminated viral cDNA such that a template-specific primer is not required; amplifying the click-ligated cDNA; and sequencing the amplicons for the whole or partial viral genome. In another aspect, the amplification reaction is a PCR, or other iso-thermal amplification reaction, or wherein the amplification step occurs without the need to design corresponding paired PCR, or other iso-thermal amplification reaction primers. In another aspect, the sequencing is by an automated process on a chip. Sanger sequencing, Maxam-Gilbert sequencing, dye terminator sequencing, sequencing by synthesis, pyrosequencing, microarray hybridization, next-generation sequencing methods, next-next-generation sequencing, ion semiconductor sequencing, polony sequencing, sequencing by ligation, DNA nanoball sequencing, or single molecule sequencing. In another aspect, the amplicons are 100-10,000 nucleotides in length. In another aspect, the method only requires one template-specific primer per amplicon. In another aspect, the sequences of the multiple tiled primer sequences are selected along the viral or bacterial genome. In another aspect, the sequences of the multiple tiled primer sequences are selected along two or more different viral or bacterial genomes in parallel. In another aspect, the sequences of the multiple tiled primer sequences only target one annealing site. In another aspect, the target nucleic acid is sequenced without the need to design corresponding paired PCR primers. In another aspect, the wherein the downstream primer comprises a unique molecular identifier. In another aspect, the downstream primer comprises a unique molecular identifier, which is a sequence such as a barcode that allows for identification of the individual downstream primer or click-adaptor. In another embodiment, the present invention includes a kit for cDNA synthesis of a genome or multiple genomes using single-primer tiled sequencing comprising, consisting essentially of, or consisting of: one or more vials comprising: four or less of terminating nucleotides of modified-deoxyGTP, modified-deoxyCTP, modified-deoxyTTP and modified-deoxyATP, dNTPs, and adaptor sequence-oligo-dT; a cDNA fragment isolating kit; one or more vials comprising components for chemically ligating a functionalized 5' adaptor to the cDNA, a DNA amplification kit comprising for amplifying the chemically-ligated cDNA into an amplification product; one or more multiple tiled primers spaced along the genome or multiple genomes, each only targeting one annealing site to form amplicons; and instructions for amplification of the RNA 3' end and one or more multiple tiled primers spaced along the genome or multiple genomes. In one aspect, the target nucleic acid is a whole viral genome or a sub-genomic viral genome or multiple genomes. In another aspect, the target nucleic acid is a whole genome or a sub-genomic genome or an RNA or DNA transcript derived from the parental genome. In another aspect, the target nucleic acid is either deoxy ribonucleic acid (DNA) or ribonucleic acid (RNA). In another aspect, the terminating modified-deoxyGTP, modified-deoxy CTP, modified-deoxyTTP and modified-deoxyATP are 2'- or 3'-azido-nucleotides (AzGTP. AzCTP, AzTTP and AzATP) or 3'-(0-Propargyl)-NTPs that pair with an alkyne or azide modified oligo during the 'click' reaction is a hexynyl-oligo or azide-oligo. In another aspect, a ratio of the four or less of 2'- or 3'-azido-nucleotides (AzGTP. AzCTP, AzTTP and AzATP), or propargyl-GTP, propargyl-CTP, propargyl-TTP or propargyl-ATP, to dNTPs is 1:250, 1:249, 1:248, 1:247, 1:246, 1:245, 1:244, 1:243, 1:242, 1:241, 1:240, 1:239, 1:238, 1:237, 1:236, 1:235, 1:234, 1:233, 1:232, 1:231, 1:230, 1:229, 1:228, 1:227, 1:226, 1:225, 1:224, 1:223, 1:222, 1:221, 1:220, 1:219, 1:218, 1:217, 1:216, 1:215, 1:214, 1:213, 1:212, 1:211, 1:210, 1:209, 1:208, 1:207, 1:206, 1:205, 1:204, 1:203, 1:202, 1:201, 1:200, 1:199, 1:198, 1:197, 1:196, 1:195, 1:194, 1:193, 1:192, 1:191, 1:190, 1:189, 1:188, 1:187, 1:186, 1:185, 1:184, 1:183, 1:182, 1:181, 1:180, 1:179, 1:178, 1:177, 1:176, 1:175, 1:174, 1:173, 1:172, 1:171, 1:170, 1:169, 1:168, 1:167, 1:166, 1:165, 1:164, 1:163, 1:162, 1:161, 1:160, 1:159, 1:158, 1:157, 1:156, 1:155, 1:154, 1:153, 1:152, 1:151, 1:150, 1:149, 1:148, 1:147, 1:146, 1:145, 1:144, 1:143, 1:142, 1:141, 1.140, 1.139, 1:138, 1:137, 1:136, 1:135, 1:134, 1:133, 1:132, 1:131, 1:130, 1:129, 1:128, 1:127, 1:126, 1:125, 1:124, 1:123, 1:122, 1:121, 1:120, 1:119, 1:118, 1:117, 1:116, 1:115, 1:114, 1:113, 1:112, 1:111, 1:110, 1:109, 1:108, 1:107, 1:106, 1:105, 1.104, 1.103, 1.102, 1:101, 1:100, 1:99, 1:98, 1:97, 1:96, 1:95, 1.94, 1:93, 1.92, 1:91, 1:90, 1:89, 1:88, 1:87, 1:86, 1:85, 1:84, 1:83, 1:82, 1:81, 1:80, 1:79, 1:78, 1:77, 1:76, 1:75, 1:74, 1:73, 1:72, 1:71, 1:70, 1:69, 1:68, 1:67, 1:66, 1:65, 1:64, 1:63, 1.62, 1:61, 1.60, 1:59, 1:58, 1:57, 1:56, 1:55, 1:54, 1:53, 1:52, 1:51, 1:50, 1.49, 1:48, 1:47, 1:46, 1:45, 1:44, 1:43, 1:42, 1:41, 1:40, 1:39, 1:38, 1:37, 1:36, 1:35, 1:34, 1:33, 1:32, 1:31, 1:30, 1:29, 1:28, 1.27, 1:26, 1:25, 1:24, 1:23, 1:22, 1:21, 1:20, 1:19, 1:18, 1:17, 1:16, 1:15, 1.14, 1:13, 1.12, 1:11, 1:10, 1:9, 1:8, 1:7, 1:6, 1:5, 1:4, 1:3, 1:2, 0.5:0.5, or 1 mM; 1 mM, or wherein a ratio of AzGTP:AzCTP:AzTTP:AzATP is w:x:y:z, wherein w is 0.1-2.0, x is 0.1-2.0, y is 0.1-2.0, and z is 0.1-2.0. In another aspect, the kit further comprises a cDNA purification kit for purifying the cDNA away from the 2' or 3'-azido-nucleotides after the reverse transcription and before the amplification step selected from a column separation kit, magnetic bead separation kit, or streptavidin magnetic bead kit. In another aspect, the kit further comprises a clicked-cDNA-adaptor purification kit for separating the clicked-cDNA-adaptor away from unligated alkyne-functionalized 5' adaptors before the amplification step selected from a column separation kit, magnetic bead separation kit, or streptavidin magnetic bead kit. In another aspect, the click-ligating components comprise: an alkyne-functionalized 5' adaptor to the azido-terminated cDNA; a buffered solution comprising: a solvent mix comprising DMSO, water, and ethanol; metal catalysts selected from copper and ruthenium; a chelating ligand; and an accelerant. In another aspect, the click-ligating components comprise: an azide-functionalized 5' adaptor to the alkyne-terminated cDNA; a buffered solution comprising a solvent mix comprising DMSO, water, and ethanol; metal catalysts selected from copper and ruthenium; a chelating ligand; and an accelerant. In another aspect, the reverse transcriptase (RT) is an RT derived from Avian Myeloblastosis Virus Reverse Transcriptase, Respiratory Syncytial Virus Reverse Transcriptase, Moloney Murine Leukemia Virus Reverse Transcriptase, Human Immunodeficiency Virus Reverse Transcriptase, Equine Infectious Anemia Virus Reverse Transcriptase, Rous-Associated Virus 2 Reverse Transcriptase, Avian Sarcoma Leukosis Virus Reverse Transcriptase, RNaseH (−) Reverse Transcriptase. SuperScript II Reverse Transcriptase, SuperScript III Reverse Transcriptase. SuperScript IV Reverse Transcriptase, thermostable group II intron reverse transcriptases (TGIRT), Therminator DNA Polymerase. or ThermoScript Reverse Transcriptase, wherein an RNase H activity of these RTs is present, reduced or not present. In another aspect, a selectivity of the reverse transcription and/or amplification, preferably a polymerase chain reaction, is increased by using trehalose, betaine, tetramethylammonium chloride, tetramethylammonium oxalate, formamide and oligo-blockers, or dimethylsulfoxide during the polymerase chain reaction, to reduce the occurrence of mispriming. In another aspect, the kit further comprises a sequencing kit determining an identity or sequence of the amplification products by an automated process on a chip. Sanger sequencing. Maxam-Gilbert sequencing, dye terminator sequencing, sequencing by synthesis, pyrosequencing, microarray hybridization, next-generation sequencing methods, next-next-generation sequencing, ion semiconductor sequencing, polony sequencing, sequencing by ligation, DNA nanoball sequencing, or single molecule sequencing. In another aspect, a DNA polymerase used for the amplification reaction is Taq DNA polymerase. Tfl DNA polymerase, a Taq DNA polymerase, a Klenow fragment, Sequenase or Klentaq an enzyme with proof reading activity, preferably selected from the PFU, Ultma, Vent, Deep Vent, PWO, or Tli polymerases. In another aspect, the kit further comprises a kit for purify ing a PCR product from the step of amplify ing the clicked-cDNA step with a column or beads. In another aspect, the wherein the downstream primer comprises a unique molecular identifier. In another aspect, the wherein the downstream primer comprises a unique molecular identifier, which is a sequence such as a barcode that allows for identification of the individual downstream primer or click-adaptor.

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one." but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited features, elements, components, groups, integers, and/or steps, but do not exclude the presence of other unstated features, elements, components, groups, integers and/or steps. In embodiments of any of the compositions and methods provided herein, "comprising" may be replaced with "consisting essentially of" or "consisting of". As used herein, the term "consisting" is used to indicate the presence of the recited integer (e.g., a feature, an element, a characteristic, a property, a method/process step or a limitation) or group of integers (e.g., feature(s), element(s), characteristic(s), property(ies), method/process steps or limitation(s)) only. As used herein, the phrase "consisting essentially of" requires the specified features, elements, components, groups, integers, and/or steps, but do not exclude the presence of other unstated features, elements, components, groups, integers and/or steps as well as those that do not materially affect the basic and novel characteristic(s) and/or function of the claimed invention.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, CABABB, and so forth. The skilled artisan will understand that typically there is no limit on the number of items or terms in any combination, unless otherwise apparent from the context.

As used herein, words of approximation such as, without limitation, "about", "substantial" or "substantially" refers to a condition that when so modified is understood to not necessarily be absolute or perfect but would be considered close enough to those of ordinary skill in the art to warrant designating the condition as being present. The extent to which the description may vary will depend on how great a change can be instituted and still have one of ordinary skill in the art recognize the modified feature as still having the required characteristics and capabilities of the unmodified feature. In general, but subject to the preceding discussion, a numerical value herein that is modified by a word of approximation such as "about" may vary from the stated value by at least 1, 2, 3, 4, 5, 6, 7, 10, 12 or 15%.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

To aid the Patent Office, and any readers of any patent issued on this application in interpreting the claims appended hereto, applicants wish to note that they do not intend any of the appended claims to invoke paragraph 6 of 35 U.S.C. § 112, U.S.C. § 112 paragraph (f), or equivalent, as it exists on the date of filing hereof unless the words "means for" or "step for" are explicitly used in the particular claim.

For each of the claims, each dependent claim can depend both from the independent claim and from each of the prior dependent claims for each and every claim so long as the prior claim provides a proper antecedent basis for a claim term or element.

REFERENCES

U.S. Patent No. 20190256547.
1. Grubaugh N D, Saraf S. Gangavarapu K, Watts A, Tan A L, Oidtman R J, et al. Travel Surveillance and Genomics Uncover a Hidden Zika Outbreak during the Waning Epidemic. Cell. 2019 Aug. 22; 178(5):1057-71 e11.
2. Gussow A B, Auslander N, Faure G, Wolf Y I, Zhang F, Koonin E V, Genomic determinants of pathogenicity in SARS-CoV-2 and other human coronaviruses. Proc Natl Acad Sci USA. 2020 Jun. 30; 117(26):15193-9.
3. Yi H. 2019 novel coronavirus is undergoing active recombination. Clin Infect Dis. 2020 Mar. 4.
4. Su Y C, Anderson D E, Young B E, Zhu F, Linster M, Kalimuddin S. et al. Discovery of a 382-nt deletion during the early evolution of SARS-CoV-2, bioRxiv. 2020; 2020.03.11.987222.
5. Muth D, Corman V M, Roth H, Binger T, Dijknan R, Gottula L T, et al. Attenuation of replication by a 29 nucleotide deletion in SARS-coronavirus acquired during the early stages of human-to-human transmission. Scientific reports. 2018 Oct. 11; 8(1):15177.
6. Kemp S. Harvey W, Datir R. Collier D, Ferreira I. Carabelli A, et al. Recurrent emergence and transmission of a SARS-CoV-2 Spike deletion ΔH69/V70, bioRxiv. 2020; 2020.12.14.422555.
7. Ogando N S, Dalebout T J, Zevenhoven-Dobbe J C, Limpens R W, van der Meer Y, Caly L, et al. SARS-coronavirus-2 replication in Vero E6 cells; replication kinetics, rapid adaptation and cytopathology, bioRxiv. 2020; 2020.04.20.049924.
8. Makino S, Taguchi F. Fujiwara K. Defective interfering particles of mouse hepatitis virus. Virology. 1984 February; 133(1):9-17.
9. Makino S, Fujioka N, Fujiwara K. Structure of the intracellular defective viral RNAs of defective interfering particles of mouse hepatitis virus. J Virol. 1985 May; 54(2):329-36.
10. Makino S, Shich C K, Keck J G, Lai M M, Defective-interfering particles of murine coronavirus: mechanism of synthesis of defective viral RNAs. Virology. 1988 March; 163(1):104-11.
11. Makino S, Shieh C K, Soe L H, Baker S C, Lai M M, Primary structure and translation of a defective interfering RNA of murine coronavirus. Virology. 1988 October; 166(2):550-60.
12. Chang R Y, Hofmann M A, Sethna P B, Brian D A. A cis-acting function for the coronavirus leader in defective interfering RNA replication. J Virol. 1994 December; 68(12):8223-31.
13. Penzes Z, Tibbles K W, Shaw K, Britton P, Brown T D, Cavanagh D, Generation of a defective RNA of avian coronavirus infectious bronchitis virus (IBV). Defective RNA of coronavirus IBV. Adv Exp Med Biol. 1995; 380: 563-9.
14. Viehweger A, Krautwurst S, Lamkiewicz K, Madhugiri R, Ziebuhr J, Holzer M, et al. Direct RNA nanopore sequencing of full-length coronavirus genomes provides novel insights into structural variants and enables modification analysis. Genome Res. 2019 09; 29(9):1545-54.
15. Banerjee S, Repass J F, Makino S, Enhanced accumulation of coronavirus defective interfering RNA from expressed negative-strand transcripts by coexpressed positive-strand RNA transcripts. Virology. 2001 Sep. 1; 287(2):286-300.
16. Joo M, Banerjee S, Makino S, Replication of murine coronavirus defective interfering RNA from negative-strand transcripts. J Virol. 1996 September; 70(9):5769-76.
17. Kim Y N, Lai M M, Makino S. Generation and selection of coronavirus defective interfering RNA with large open reading frame by RNA recombination and possible editing. Virology. 1993 May; 194(1):244-53.
18. Gribble J, Pruijssers A J, Agostini M L, Anderson-Daniels J, Chappell J D, Lu X, et al. The coronavirus proofreading exoribonuclease mediates extensive viral recombination, bioRxiv. 2020:2020.04.23.057786.
19. Vignuzzi M, Lopez C B. Defective viral genomes are key drivers of the virus-host interaction. Nat Microbiol. 2019 Jun. 3.
20. Tyson J R, James P, Stoddart D, Sparks N, Wickenhagen A, Hall G, et al. Improvements to the ARTIC multiplex PCR method for SARS-CoV-2 genome sequencing using nanopore, bioRxiv. 2020 Sep. 4.
21. Grubaugh N D, Gangavarapu K, Quick J, Matteson N L, De Jesus J G, Main B J, et al. An amplicon-based sequencing framework for accurately measuring intrahost virus diversity using PrimalSeq and iVar. Genome Biol. 2019 Jan. 8; 20(1):8.
22. Routh A, Head S R, Ordoukhanian P, Johnson J E. ClickSeq: Fragmentation-Free Next-Generation Sequencing via Click Ligation of Adaptors to Stochastically Terminated 3'-Azido cDNAs. J Mol Biol. 2015 Jun. 24.
23. Jaworski E, Routh A. ClickSeq: Replacing Fragmentation and Enzymatic Ligation with Click-Chemistry to Prevent Sequence Chimeras. Methods Mol Biol. 2018; 1712:71-85.
24. Gorzer I, Guelly C. Trajanoski S, Puchhammer-Stockl E. The impact of PCR-generated recombination on diversity estimation of mixed viral populations by deep sequencing. J Virol Methods. 2010 October; 169(1):248-52.

25. Itokawa K, Sekizuka T, Hashino M, Tanaka R. Kuroda M. Disentangling primer interactions improves SARS-CoV-2 genome sequencing by multiplex tiling PCR. PloS one. 2020; 15(9):e0239403.
26. Harcourt J, Tamin A, Lu X, Karnili S, Sakthivel S K, Murray J, et al. Severe Acute Respiratory Syndrome Coronavirus 2 from Patient with Coronavirus Disease, United States. Emerg Infect Dis. 2020 June; 26(6):1266-73.
27. Xie X, Muruato A, Lokugamage K G, Narayanan K, Zhang X, Zou J, et al. An Infectious cDNA Clone of SARS-CoV-2. Cell Host Microbe. 2020 May 13; 27(5): 841-8 e3.
28. Johnson B A, Xie X, Bailey A L, Kalveram B, Lokugamage K G, Muruato A, et al. Loss of furin cleavage site attenuates SARS-CoV-2 pathogenesis. Nature. 2021 Jan. 25.
29. Guo L, Boocock J, Tome J M, Chandrasekaran S, Hilt E E, Zhang Y. et al. Rapid cost-effective viral genome sequencing by V-seq, bioRxiv. 2020:2020.08.15.252510.
30. Routh A, Head S R, Ordoukhanian P, Johnson J E. ClickSeq: Fragmentation-Free Next-Generation Sequencing via Click Ligation of Adaptors to Stochastically Terminated 3'-Azido cDNAs. J Mol Biol. 2015 Aug. 14:427(16):2610-6.
31. Chen S, Zhou Y, Chen Y, Gu J, fastp: an ultra-fast all-in-one FASTQ preprocessor. Bioinformatics. 2018:34 (17):i884-i90.
32. Martin M. Cutadapt removes adapter sequences from high-throughput sequencing reads. EMBnetjournal. 2011; 17:10-2.
33. Langmead B, Salzberg S L. Fast gapped-read alignment with Bowtie 2. Nature methods. 2012 Mar. 4; 9(4):357-9.
34. Walker B J, Abeel T, Shea T, Priest M, Abouelliel A, Sakthikumar S, et al. Pilon: an integrated tool for comprehensive microbial variant detection and genome assembly improvement. PloS one. 2014; 9(11):c112963.
35. Routh A, Johnson J E. Discovery of functional genomic motifs in viruses with ViReMa-a Virus Recombination Mapper—for analysis of next-generation sequencing data. Nucleic Acids Res. 2014 January; 42(2):e 11.
36. Li H, Handsaker B, Wysoker A, Fennell T, Ruan J, Homer N, et al. The Sequence Alignment/Map format and SAMtools. Bioinformatics. 2009 Aug. 15; 25(16):2078-9.
37. Smith T. Heger A, Sudbery I. UMI-tools: modeling sequencing errors in Unique Molecular Identifiers to improve quantification accuracy. Genome Res. 2017 March; 27(3):491-9.
38. Milne 1, Bayer M, Cardle L, Shaw P, Stephen G, Wright F, et al. Tablet-next generation sequence assembly visualization. Bioinfornatics. 2010 Feb. 1:26(3):401-2.
39. Li H, Minimap and miniasm: fast mapping and de novo assembly for noisy long sequences. Bioinformatics. 2016 Jul. 15:32(14):2103-10.
40. Quinlan A R. BEDTools: The Swiss-Army Tool for Genome Feature Analysis. Curr Protoc Bioinformatics. 2014 Sep. 8:47:112 1-34.
41. Routh A, Ji P, Jaworski E, Xia Z, Li W, Wagner E J. Poly(A)-ClickSeq: click-chemistry for next-generation 3-end sequencing without RNA enrichment or fragmentation. Nucleic Acids Res. 2017 Jul. 7; 45(12):e112.
42. Jabara C B, Jones C D, Roach J, Anderson J A, Swanstrom R. Accurate sampling and deep sequencing of the HIV-1 protease gene using a Primer ID. Proc Natl Acad Sci USA. 2011 Dec. 13; 108(50):20166-71.
43. Harcourt J, Tamin A, Lu X, Kamili S, Sakthivel S K, Murray J, et al. Isolation and characterization of SARS-CoV-2 from the first US COVID-19 patient, bioRxiv. 2020 Mar. 7.
44. Plante J A, Liu Y, Liu J, Xia H, Johnson B A, Lokugamage K G, et al. Spike mutation D614G alters SARS-CoV-2 fitness and neutralization susceptibility, bioRxiv. 2020 Sep. 2.
45. Hadfield J, Megill C, Bell S M, Huddleston J, Potter B, Callender C, et al. Nextstrain: real-time tracking of pathogen evolution. Bioinformatics. 2018 Dec. 1; 34(23):4121-3.
46. Kim D, Lee J Y, Yang J S, Kim J W, Kim V N, Chang H. The Architecture of SARS-CoV-2 Transcriptome. Cell. 2020 Apr. 18.
47. Klinstra W B, Tilston-Lunel N L, Nambulli S, Boslett J, McMillen C M, Gilliland T, et al. SARS-CoV-2 growth, furin-cleavage-site adaptation and neutralization using serum from acutely infected, hospitalized COVID-19 patients, bioRxiv. 2020:2020.06.19.154930.
48. Gribble J, Stevens U, Agostini M L, Anderson-Daniels J, Chappell J D, Lu X, et al. The coronavirus proofreading exoribonuclease mediates extensive viral recombination. PLoS pathogens. 2021 January; 17(1):e1009226.
49. Plante J A, Mitchell B M, Plante K S, Debbink K, Weaver S C, Menachery V D. The Variant Gambit: COVID's Next Move. Cell Host & Microbe. 2021 2021/03/01/.
50. Smith E C, Denison M R. Coronaviruses as DNA wannabes: a new model for the regulation of RNA virus replication fidelity. PLoS pathogens. 2013; 9(12): e1003760.
51. Knyazev S, Tsyvina V, Shankar A, Melnyk A, Artyomenko A, Malygina T. et al. CliqueSNV: An Efficient Noise Reduction Technique for Accurate Assembly of Viral Variants from NGS Data, bioRxiv. 2020:264242.
52. Routh A, Chang M W, Okulicz J F, Johnson J E, Torbett B E. CoVaMa: Co-Variation Mapper for disequilibrium analysis of mutant loci in viral populations using next-generation sequence data. Methods. 2015 Sep. 25.
53. Parker M D, Lindsey B B, Leary S, Gaudieri S, Chopra A, Wyles M, et al. periscope: sub-genomic RNA identification in SARS-CoV-2 Genomic Sequencing Data, bioRxiv. 2020:2020.07.01.181867.

What is claimed is:

1. A method of single-primer-per-amplicon tiled sequencing comprising:
reverse transcribing a target nucleic acid with multiple tiled primers, random primers, or both, spaced along a genome, each only targeting one annealing site to form amplicons, in the presence of terminating 3' azido nucleotides to incorporate the terminating 3' azido nucleotides into the cDNA;
click-ligating a downstream adaptor onto the 3' azido terminated cDNA without template-specific primers;
amplifying the click-ligated cDNA; and
sequencing the amplicons.

2. The method of claim 1, wherein the target nucleic acid is:
a partial or whole viral or bacterial genome, a sub-genomic viral genome, or
RNA or DNA transcript derived from the parental genome.

3. The method of claim 1, wherein the amplification reaction is selected from the group consisting of: a PCR, an iso-thermal amplification reaction, and an amplification reaction without the need to design corresponding paired PCR or iso-thermal amplification reaction primers.

4. The method of claim 1, wherein the sequencing is selected from the group consisting of an automated process on a chip, Sanger sequencing, Maxam-Gilbert sequencing, dye terminator sequencing, sequencing by synthesis, pyrosequencing, microarray hybridization, next-generation sequencing methods, next-next-generation sequencing, ion semiconductor sequencing, polony sequencing, sequencing by ligation, DNA nanoball sequencing, and single molecule sequencing.

5. The method of claim 1, wherein amplicons are 100-10,000 nucleotides in length.

6. The method of claim 1, wherein sequences of the multiple tiled primer sequences is selected from the group consisting of:
selected along a virus genome; and
selected along two or more different viral or bacterial genomes in parallel.

7. The method of claim 1, wherein the target nucleic acid is sequenced without the need to design corresponding paired PCR primers.

8. The method of claim 1, wherein the downstream primer comprises a unique molecular identifier.

9. A method of single-primer tiled sequencing comprising:
reverse transcribing a target nucleic acid with multiple tiled primers, random primers, or both, spaced along the whole or partial viral or bacterial genome or genomes, each only targeting one annealing site to form amplicons, in the presence of terminating 3' azido nucleotides to incorporate the terminating 3' azido nucleotides into the cDNA;
click-ligating a downstream adaptor onto the 3' azido terminated target cDNA without template-specific primers;
amplifying the click-ligated cDNA; and
sequencing the amplicons for the whole or partial target genome.

10. The method of claim 9, wherein the amplification reaction is selected from the group consisting of: a PCR, an iso-thermal amplification reaction, and an amplification reaction without the need to design corresponding paired PCR or other iso-thermal amplification reaction primers.

11. The method of claim 9, wherein the sequencing is selected from the group consisting of an automated process on a chip, Sanger sequencing, Maxam-Gilbert sequencing, dye terminator sequencing, sequencing by synthesis, pyrosequencing, microarray hybridization, next-generation sequencing methods, next-next-generation sequencing, ion semiconductor sequencing, polony sequencing, sequencing by ligation, DNA nanoball sequencing, and single molecule sequencing.

12. The method of claim 9, wherein amplicons are 100-10,000 nucleotides in length.

13. The method of claim 9, wherein sequences of the multiple tiled primer sequences are selected from the group consisting of:
selected along the viral or bacterial genome; and
selected along two or more different viral or bacterial genomes in parallel.

14. The method of claim 9, wherein the target nucleic acid is sequenced without the need to design corresponding paired PCR primers.

15. The method of claim 9, wherein the downstream adaptor comprises a unique molecular identifier.

16. The method of claim 1, wherein the target nucleic acid is a metazoan RNA or a messenger RNA.

17. The method of claim 1, wherein the target nucleic acid is a ribonucleic acid (RNA).

* * * * *